(12) United States Patent
Duggal et al.

(10) Patent No.: US 12,026,481 B2
(45) Date of Patent: *Jul. 2, 2024

(54) SYSTEMS AND METHODS FOR CREATING SOFTWARE FROM LIBRARY AND CUSTOM COMPONENTS

(71) Applicant: Engineer.ai Global Limited, London (GB)

(72) Inventors: Sachin Dev Duggal, Los Angeles, CA (US); Rohan Patel, Los Angeles, CA (US)

(73) Assignee: Engineer.ai Global Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/721,992

(22) Filed: Apr. 15, 2022

(65) Prior Publication Data

US 2022/0244923 A1 Aug. 4, 2022

Related U.S. Application Data

(63) Continuation of application No. 17/380,456, filed on Jul. 20, 2021, which is a continuation of application
(Continued)

(51) Int. Cl.
*G06F 9/44* (2018.01)
*A61M 21/02* (2006.01)
(Continued)

(52) U.S. Cl.
CPC .............. *G06F 8/316* (2013.01); *A61M 21/02* (2013.01); *G06F 8/20* (2013.01); *G06F 8/36* (2013.01);
(Continued)

(58) Field of Classification Search
CPC .. A61M 2021/0016; A61M 2021/0022; A61M 21/02; G06F 8/20; G06F 8/316;
(Continued)

(56) References Cited

U.S. PATENT DOCUMENTS

| 6,016,394 A | 1/2000 | Walker |
| 6,697,824 B1 | 2/2004 | Bowman-Amuah |

(Continued)

FOREIGN PATENT DOCUMENTS

KR 101975272 B1 5/2019

OTHER PUBLICATIONS

Sharlene Aminullah, "Cost Estimation of Service Delivery in Cloud Computing", Aug. 2012, Arjuna Technologies Ltd., 95 pages. (Year: 2012).*

(Continued)

*Primary Examiner* — Ted T. Vo
(74) *Attorney, Agent, or Firm* — Fox Rothschild LLP

(57) ABSTRACT

Methods and systems are disclosed that automate and institutionalize many aspects of the process of creating software. Embodiments automate aspects of pricing, software creation, and delivery using a manufacturing-styled approach to development that reuses existing code and other existing software design features.

18 Claims, 42 Drawing Sheets

Engineer.ai System Architecture

Related U.S. Application Data

No. 16/854,805, filed on Apr. 21, 2020, now Pat. No. 11,086,599, which is a continuation of application No. 15/786,431, filed on Oct. 17, 2017, now Pat. No. 10,649,741.

(60) Provisional application No. 62/408,935, filed on Oct. 17, 2016.

(51) Int. Cl.

| | | |
|---|---|---|
| *G06F 8/20* | (2018.01) | |
| *G06F 8/30* | (2018.01) | |
| *G06F 8/36* | (2018.01) | |
| *G06F 8/71* | (2018.01) | |
| *G06Q 10/0631* | (2023.01) | |
| *G06Q 30/0283* | (2023.01) | |
| *A61M 21/00* | (2006.01) | |

(52) U.S. Cl.
CPC ......... *G06F 8/71* (2013.01); *G06Q 10/06311* (2013.01); *G06Q 30/0283* (2013.01); *A61M 2021/0016* (2013.01); *A61M 2021/0022* (2013.01)

(58) Field of Classification Search
CPC ....... G06F 8/36; G06F 8/71; G06Q 10/06311; G06Q 30/0283
USPC .......................................................... 717/107
See application file for complete search history.

(56) References Cited

U.S. PATENT DOCUMENTS

| | | |
|---|---|---|
| 7,783,523 B2 | 8/2010 | Lopez |
| 8,458,009 B1 | 6/2013 | Southworth |
| 8,621,423 B2 | 12/2013 | Knight |
| 9,286,040 B2 | 3/2016 | Halley |
| 10,649,741 B2 | 5/2020 | Duggal |
| 2003/0018952 A1 | 1/2003 | Roetzheim |
| 2005/0066304 A1 | 3/2005 | Tattrie et al. |
| 2006/0259442 A1 | 11/2006 | Iqbal |
| 2008/0004844 A1 | 1/2008 | Kefford |
| 2008/0235155 A1 | 9/2008 | Thywissen |
| 2009/0037287 A1 | 2/2009 | Baitalmal |
| 2011/0088011 A1 | 4/2011 | Ouali |
| 2011/0276354 A1 | 11/2011 | Bijani et al. |
| 2012/0331439 A1 | 12/2012 | Zimmermann et al. |
| 2016/0055079 A1 | 2/2016 | Hanna |
| 2016/0092179 A1 | 3/2016 | Straub |

OTHER PUBLICATIONS

Nathan Curtis, "Modular Web Design—Creating Reusable Components for User Experience Design", 2010, Peachpit Press, 328 pages. (Year: 2010).*

Dekkers, "Beyond Development: Estimating Model for Run & Maintain Cost", 2007, Software Measurement European Forum, Italy, pp. 249-264. (Year: 2007).*

Notification of Transmittal of the International Search Report and the Written Opinion of the International Searching Authority, or the Declaration for International Application No. PCT/US2017/057030, International Filing Date Oct. 17, 2017, dated Jan. 4, 2018, 7 pages.

Angel Puerta et al., "The UI Pilot: A Model-Based Tool to Guide Early Interface Design", 2005, ACM, pp. 215-222 (Year: 2005).

International Search Report and the Written Opinion, International Application No. PCT/EP2020/085866, dated Mar. 31, 2021 (11 poages).

Al Asheeri and Hammad, "Machine Learning Models for Software Cost Estimation," 2019 International Conference on Innovation and Intelligence for Informatics, Computing, and Technologies (3ICT), 6 pages (2019).

* cited by examiner

Full stack solution

S.I.M.B.A
The friendly A.I.

Engineer.ai

- Automated pricing
- Machine assisted product management
- Code creation

SD SQUARED

The user is now presented with an initial price based on both platforms that need to be built and the number of estimated screens. The price projection dynamically changes based on the user selections.

| Engineer.ai | What | Type | | $33,026.00 |
|---|---|---|---|---|
| | Mobile Apps | Yelp | | |

Personalize your app

Pick a category. If you can't find what you are looking for for "Choose 'Something else'" and we will connect you to a concierge straight away

Platforms

Select Platforms

- Android — $636.00
- iOS — $639.00
- Web — $636.00

Number of screens

- 5-10 — $290.00
- 10-20 — $460.00
- 20-35 — $660.00
- Don't know — $499.00

[ Next > ]

FIG. 27

The user is now presented with the default features that map to the type of application / product they selected. The user can select or deselect on a feature by feature basis. The price projection dynamically reflects this.

| Engineer.ai | What<br>Mobile Apps | Type<br>Yelp | | $41,020.00 |
|---|---|---|---|---|

Personalize your app

Pick a category, if you can't find what you are looking for tic "choose 'Something else' and we will connect you to a concierge straight away

Platforms

Select Features
5 selected

Login $100.00
Profile $100.00
Analytics $75.00
Search $85.00
Location $125.00

Notifications $50.00
Share $100.00
Comments $150.00
Videos $100.00
Photos $130.00

( Next > )

SYSTEMS AND METHODS FOR CREATING SOFTWARE FROM LIBRARY AND CUSTOM COMPONENTS

CROSS-REFERENCE TO RELATED APPLICATIONS

This Application is a Continuation of application Ser. No. 17/380,456 filed on Jul. 20, 2021. Application Ser. No. 17/380,456 is a Continuation of application Ser. No. 16/854,805 filed on Apr. 21, 2020. Application Ser. No. 16/854,805 is a Continuation of application Ser. No. 15/786,431 filed on Oct. 17, 2017. Application Ser. No. 15/786,431 claims the benefit of U.S. Provisional Application 62/408,935 filed on Oct. 17, 2016. The entire contents of these applications are incorporated herein by reference in their entirety.

TECHNICAL FIELD

The claimed subject matter relates to the field of software, and more particularly to the creation of software from library components and custom components.

BRIEF DESCRIPTION OF THE FIGURES

FIGS. 18-37 describe and illustrate a user experience and flow using screenshots from a user interface of an embodiment for creating software; and FIGS. 38-43 describe and illustrate an administrative user interface and flow using screenshots of an embodiment for creating software.

DETAILED DESCRIPTION

Figure 1:
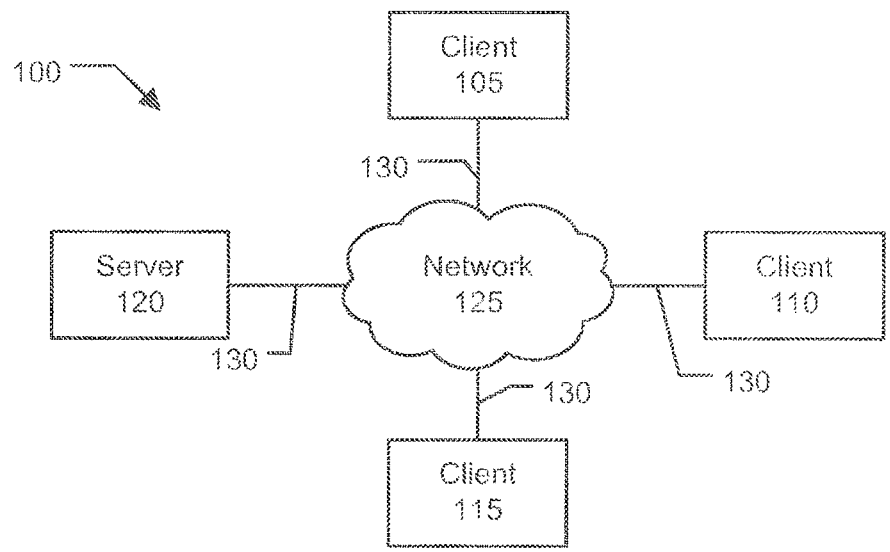
FIG. 1 shows a simplified block diagram of an embodiment of a system for creating software.

FIG. 1 is a simplified block diagram of a distributed computer network 100 incorporating an embodiment of the present invention. Computer network 100 includes a number of client systems 105, 110, and 115, and a server system 120 coupled to a communication network 125 via a plurality of communication links 130. Communication network 125 provides a mechanism for allowing the various components of distributed network 100 to communicate and exchange information with each other.

Communication network 125 may itself be comprised of many interconnected computer systems and communication links. Communication links 130 may be hardwire links, optical links, satellite or other wireless communications links, wave propagation links, or any other mechanisms for communication of information. Various communication protocols may be used to facilitate communication between the various systems shown in FIG. 1. These communication protocols may include TCP/IP, HTTP protocols, wireless application protocol (WAP), vendor-specific protocols, customized protocols, and others. While in one embodiment, communication network 125 is the Internet, in other embodiments, communication network 125 may be any suitable communication network including a local area network (LAN), a wide area network (WAN), a wireless network, a intranet, a private network, a public network, a switched network, Internet telephony. IP telephony, digital voice, voice over broadband (VoBB), broadband telephony, Voice over IP (VoIP), public switched telephone network (PSTN), and combinations of these, and the like.

System 100 in FIG. 1 is merely illustrative of an embodiment and does not limit the scope of the systems and methods as recited in the claims. One of ordinary skill in the art would recognize other variations, modifications, and alternatives. For example, more than one server system 120 may be connected to communication network 125. As another example, a number of client systems 105, 110, and 115 may be coupled to communication network 125 via an access provider (not shown) or via some other server system. An instance of a server system 120 and a computing device 105 may be part of the same or a different hardware system. An instance of a server system 120 may be operated by a provider different from an organization operating an embodiment of a system for specifying an object in a design, or may be operated by the same organization operating an embodiment of a system for specifying an object in a design.

Client systems 105, 110, and 115 typically request information from a server system which provides the information. Server systems by definition typically have more computing and storage capacity than client systems. However, a particular computer system may act as both a client and a server depending on whether the computer system is requesting or providing information. Aspects of the system may be embodied using a client-server environment or a cloud-cloud computing environment.

Server 120 is responsible for receiving information requests from client systems 105, 110, and 115, performing processing required to satisfy the requests, and for forwarding the results corresponding to the requests back to the requesting client system. The processing required to satisfy the request may be performed by server system 120 or may alternatively be delegated to other servers connected to communication network 125.

Client systems 105, 110, and 115 enable users to access and query information or applications stored by server system 120. Some example client systems include portable electronic devices (e.g., mobile communication devices) such as the Apple iPhone®, the Apple iPad®, the Palm Pre™, or any device running the Apple iOS™, Android™ OS, Google Chrome OS, Symbian OS®, Windows Mobile® OS, Palm OS® or Palm Web OS™. In a specific embodiment, a "web browser" application executing on a client system enables users to select, access, retrieve, or query information and/or applications stored by server system 120. Examples of web browsers include the Android browser provided by Google, the Safari® browser provided by Apple, the Opera Web browser provided by Opera Software, the BlackBerry® browser provided by Research In Motion, the Internet Explorer® and Internet Explorer Mobile browsers provided by Microsoft Corporation, the Firefox® and Firefox for Mobile browsers provided by Mozilla®, and others.

Figure 2:
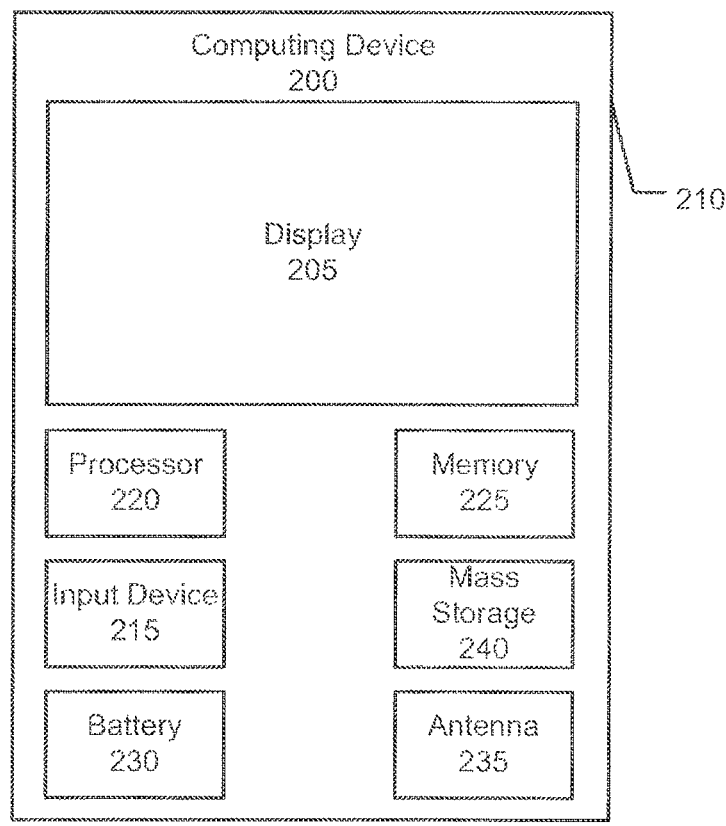
FIG. 2 shows a more detailed diagram of an example of a computing device from a system for creating software.

FIG. 2 shows an exemplary computer system such as a client system of the present invention. In an embodiment, a user interfaces with the system through a client system, such as shown in FIG. 2. Mobile client communication or portable electronic device 200 includes a display, screen, or monitor 205, housing 210, and input device 215. Housing 210 houses familiar computer components, some of which are not shown, such as a processor 220, memory 225, battery 230, speaker, transceiver, antenna 235, microphone, ports, jacks, connectors, camera, input/output (I/O) controller, display adapter, network interface, mass storage devices 240, and the like. Computer system 200 may include a bus or other communication mechanism for communicating information between components. Mass storage devices 240 may store a user application and system software components. Memory 225 may store information and instructions to be executed by processor 220.

Input device 215 may also include a touchscreen (e.g., resistive, surface acoustic wave, capacitive sensing, infrared, optical imaging, dispersive signal, or acoustic pulse recognition), keyboard (e.g., electronic keyboard or physical keyboard), buttons, switches, stylus, gestural interface (contact or non-contact gestures), biometric input sensors, or combinations of these.

Mass storage devices 240 may include flash and other nonvolatile solid-state storage or solid-state drive (SSD), such as a flash drive, flash memory, or USB flash drive. Other examples of mass storage include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), battery-backed-up volatile memory, tape storage, reader, and other similar media, and combinations of these.

System 100 may also be used with computer systems having different configurations, e.g., with additional or fewer subsystems. For example, a computer system could include more than one processor (i.e., a multiprocessor system, which may permit parallel processing of information) or a system may include a cache memory. The computer system shown in FIG. 2 is but an example of a computer system suitable for use. Other configurations of subsystems suitable for use will be readily apparent to one of ordinary skill in the art. For example, in a specific implementation, the computing device is mobile communication device such as a smartphone or tablet computer. Some specific examples of smartphones include the Droid Incredible and Google Nexus One®, provided by HTC Corporation, the iPhone® or iPad®, both provided by Apple, BlackBerry Z10 provided by BlackBerry (formerly Research In Motion), and many others. The computing device may be a laptop or a netbook. In another specific implementation, the computing device is a non-portable computing device such as a desktop computer or workstation.

A computer-implemented or computer-executable version of the program instructions useful to practice the present invention may be embodied using, stored on, or associated with computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software useful to practice the present invention may be stored or reside in RAM or cache memory, or on mass storage device 240. The source code of this software may also be stored or reside on mass storage device 240 (e.g., flash drive, hard disk, magnetic disk, tape, or CD-ROM). As a further example, code useful for practicing the invention may be transmitted via wires, radio waves, or through a network such as the Internet. In another specific embodiment, a computer program product including a variety of software program code to implement features of the invention is provided.

Computer software products may be written in any of various suitable programming languages, such as C, C++, C#, Pascal, Fortran, Perl, Matlab (from MathWorks, www-.mathworks.com), SAS, SPSS, JavaScript, CoffeeScript, Objective-C, Objective-J, Ruby, Python, Erlang, Lisp, Scala, Clojure, and Java. The computer software product may be an independent application with data input and data display modules. Alternatively, the computer software products may be classes that may be instantiated as distributed objects. The computer software products may also be component software such as Java Beans (from Oracle) or Enterprise Java Beans (EJB from Oracle).

An operating system for the system may be the Android operating system, iPhone OS (i.e., iOS), Symbian, BlackBerry OS, Palm web OS, bada, MeeGo, Maemo, Limo, or Brew OS. Other examples of operating systems include one of the Microsoft Windows family of operating systems (e.g., Windows 95, 98, Me, Windows NT, Windows 2000, Windows XP, Windows XP x64 Edition, Windows Vista, Windows 7, Windows CE, Windows Mobile, Windows Phone 7), Linux, HP-UX, UNIX, Sun OS, Solaris, Mac OS X. Alpha OS, AIX, IRIX32, or IRIX64. Other operating systems may be used.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system useful in practicing the invention using a wireless network employing a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

Figure 3:
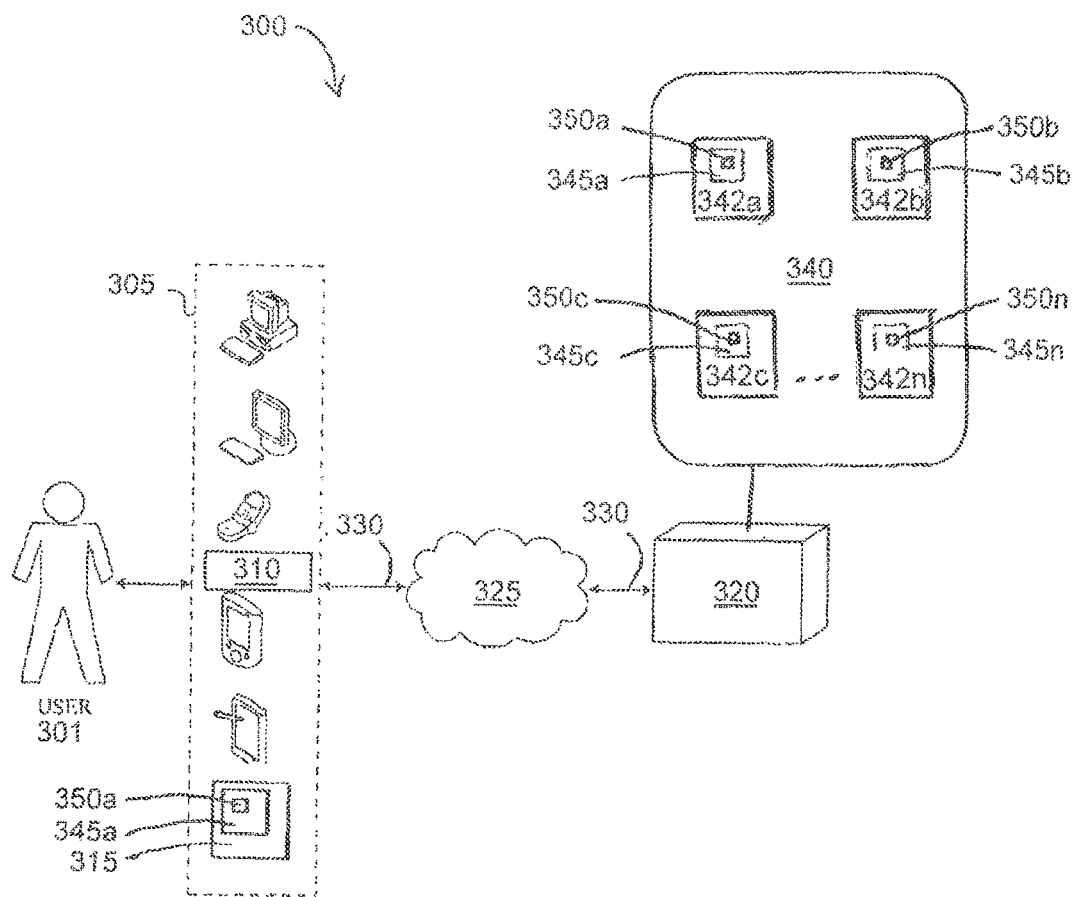
FIG. 3 is a simplified block diagram of an embodiment of a system for creating software.

FIG. 3 is a simplified block diagram of an embodiment of a system 300 for creating software for use by a user 301. System 300 includes one or more user computing devices 305, and a server 320, coupled to a communication network 325 via a plurality of communication links 330. Computing device 305 may be used to run a user application 310 for creating software from existing code and new code. User application 310 may use computing device 305 and network 325 to access server 320. Communication network 325 (or "network 325") provides a mechanism for allowing the various components of system 300 to communicate and exchange information with each other via communication links 330. Server 320 may include or have access to a database 340 of code libraries 342a, 342b, . . . , 342n. Each code library includes software code (not shown) from which system 300 may select to create customized software. Each code library 342a, 342b, . . . , 342n may have selected from it a subset of code sections 345a, 345b, . . . , 345n, which server 320 may assemble into customized software 350a, 350b, . . . , 350n and provide to user 301 via computing device 305. Customized software may be complete or may need to be augmented with additional custom code sections that may be newly created by partner developers. Server 320 or an administrator may combine or integrate newly created code with existing code sections to create customized software.

Computing device 305 may run a software-creating component 315 which may be provided with a subset of code sections (e.g., subset 345a from server 320 via user application 310) that software-creating component 315 (like server 320) may assemble into customized software (e.g., customized software 350a).

Network 325 may be any suitable communications network. Communication network 325 may itself be comprised of many interconnected computer systems and communication links. As an example and not by way of limitation, one or more portions of network 325 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, another suitable network, or a combination of two or more of these. Network 325 may include one or more networks 325.

Connections 330 may connect computing device 305 and server 320 to communication network 325 or to each other. Communication links 330 may be hardwire links, optical links, satellite or other wireless communications links, wave propagation links, or any other mechanisms for communication of information. This disclosure contemplates any suitable connections 325. In particular embodiments, one or more connections 325 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)) or optical (such as for example Synchronous Optical Network (SONET) or Synchronous Digital Hierarchy (SDH)) connections. In particular embodiments, one or more connections 330 each include an ad hoc network, an intranet, an extranet, a VPN, a LAN, a WLAN, a WAN, a WWAN, a MAN, a portion of the Internet, a portion of the PSTN, a cellular telephone network, another suitable connection 330, or a combination of two or more such connections 330. Connections 330 need not necessarily be the same throughout system 300. One or more first connections 330 may differ in one or more respects from one or more second connections 330.

Server 320 may be a network-addressable computing system that can host one or more product databases 340.

Server 320 may be responsible for receiving information requests from computing device 305 via user application 310, for performing the processing required to satisfy the requests, for generating responses (e.g., custom software 350a, . . . , 350n) to received inquiries, and for forwarding the results corresponding to the requests back to requesting computing device 305. Server 320 may store, receive, or transmit data and software, and information associated with the data and software (including user data). The processing required to satisfy the requests may be performed by server 320 or may alternatively be delegated to other servers connected to communication network 325. For example, other servers may host database 340, or have additional databases. Server 320 may be an intermediary in communications between a computing device 305 and another server system, or a computing device 305 may communicate directly with another server system. Server 320 may be accessed by the other components of system 300, for example, directly or via network 325. In particular embodiments, one or more users 301 may use one or more computer devices 305 to access, send data to, and receive data from server 320.

Computing device 305, connections 330, and network 325, enable user 301 to access and query information stored and applications run by server 320, such as database 340. Some example computer devices 305 include desktop computers, portable electronic devices (e.g., mobile communication devices, smartphones, tablet computers, laptops) such as the Samsung Galaxy Tab®, Google Nexus devices, Amazon Kindle®, Kindle Fire®, Apple iPhone®, the Apple iPad®, Microsoft Surface®, the Palm Pre™, or any device running the Apple iOS®, Android® OS, Google Chrome® OS, Symbian OS®, Windows Mobile® OS, Windows Phone, BlackBerry® OS, Embedded Linux, Tizen, Sailfish, webOS, Palm OS® or Palm Web OS®.

In an embodiment, user application 310 may be run or executed by a different system. For example, computing device 305, or server 320, or both, may run user application 310. That is, user application 310 may be run by computing device 305, or the application may be run on server 320 and accessed by computing device 305 through a browser and network 325. For example, computing device 305 could be operated as a terminal, with user application 310 being run on a server, e.g., server 320. In an embodiment, aspects or functionalities of user application 310 are run by server 320, or another computing system or server. In an embodiment, the steps of the methods described herein may be performed, at least in part, in cloud-computing environment.

FIG. 3 illustrates a particular arrangement of user 301, computing device 305, and server 320, but this is an example arrangement. Any other suitable arrangement of user 301, computing device 305, server 320, and network 325 may be used. For example, computing device 305 may be connected directly to server 320. Also, computing device 305 and server 320 may appear to be distinct yet operate on the same hardware. In addition, any number of users 301, clients 305, and server 320 may be used in embodiments.

Figure 4:
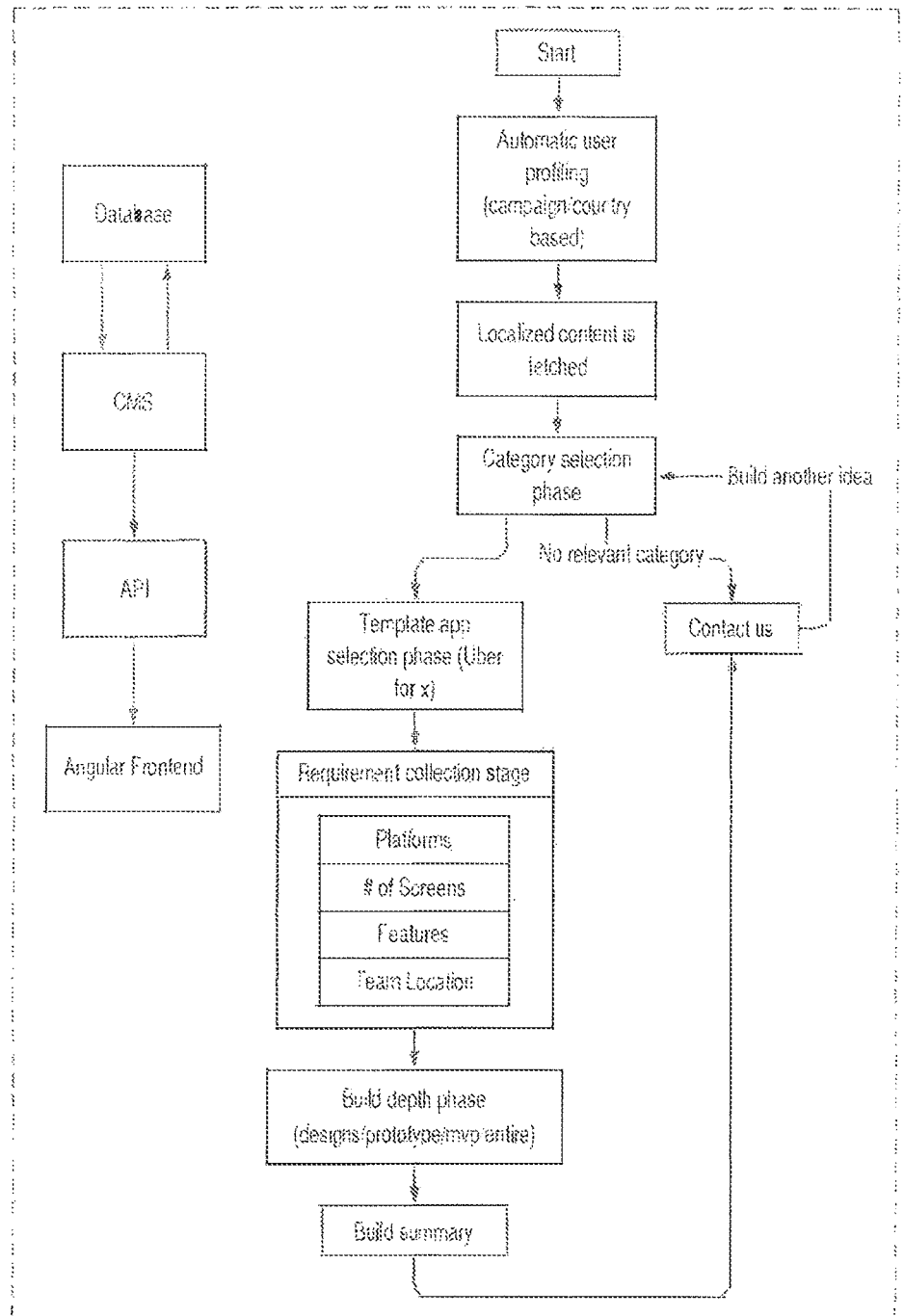
FIG. 4 is a diagram showing a block diagram of aspects of system architecture of an embodiment for creating software, i.e., decision triggers and user flow, and a block diagram illustrating back end components of an embodiment for creating software.
Figure 5:
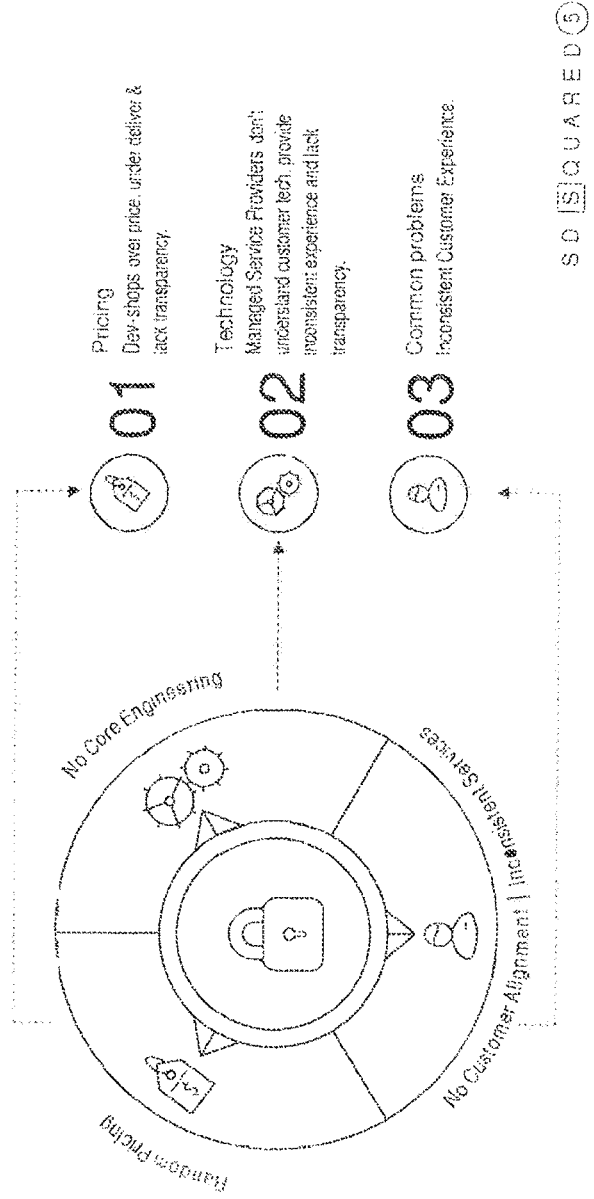
FIGS. 5-10 describe and illustrate aspects of the problem and the solution to the problem provided by embodiments of the systems and methods.
Figure 6:
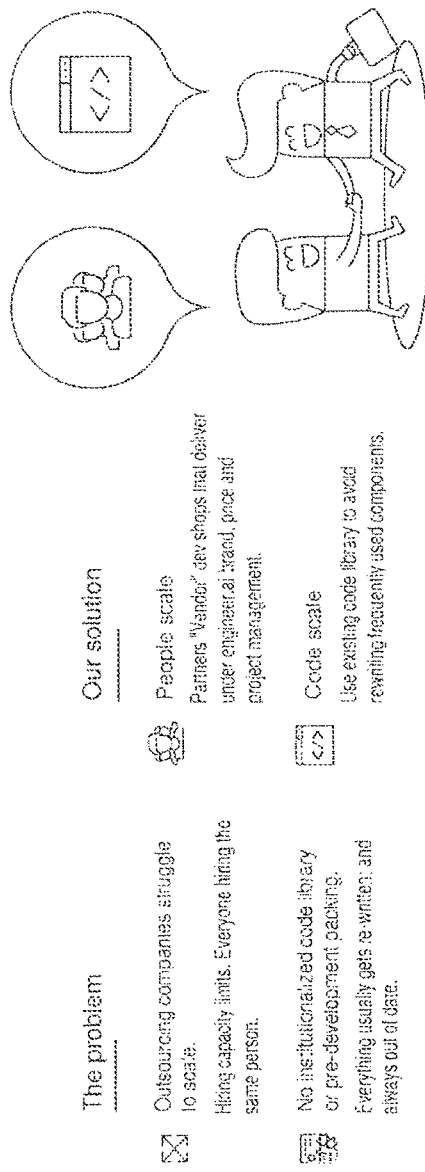
Figure 7:
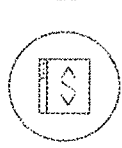
Figure 8:
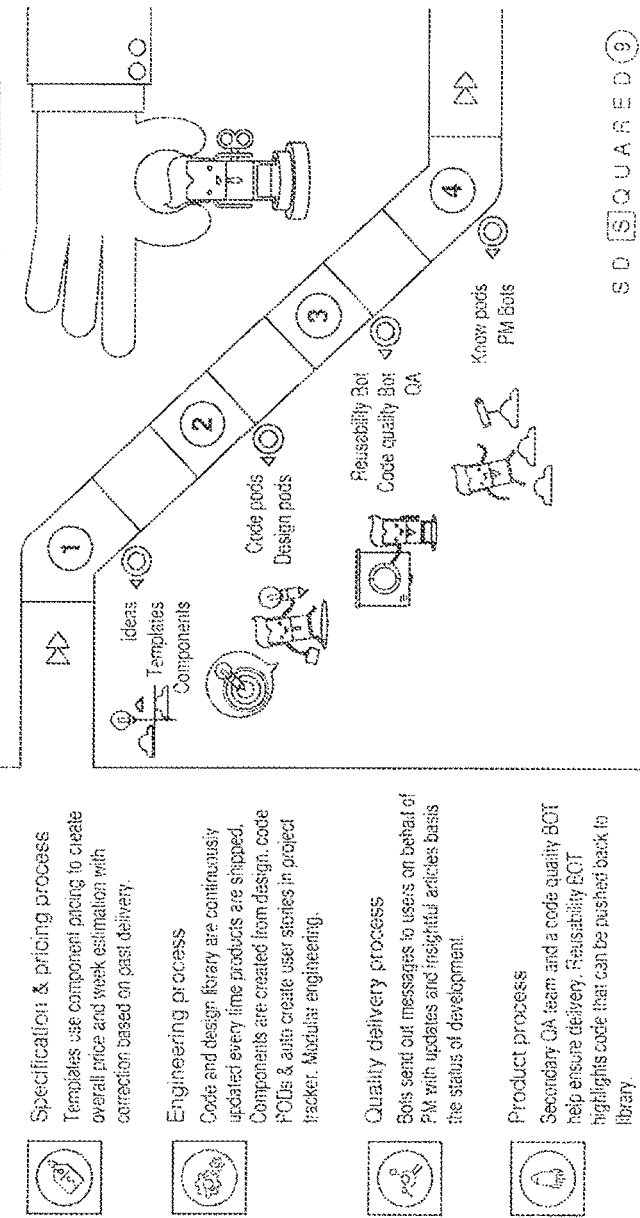
Figure 9:
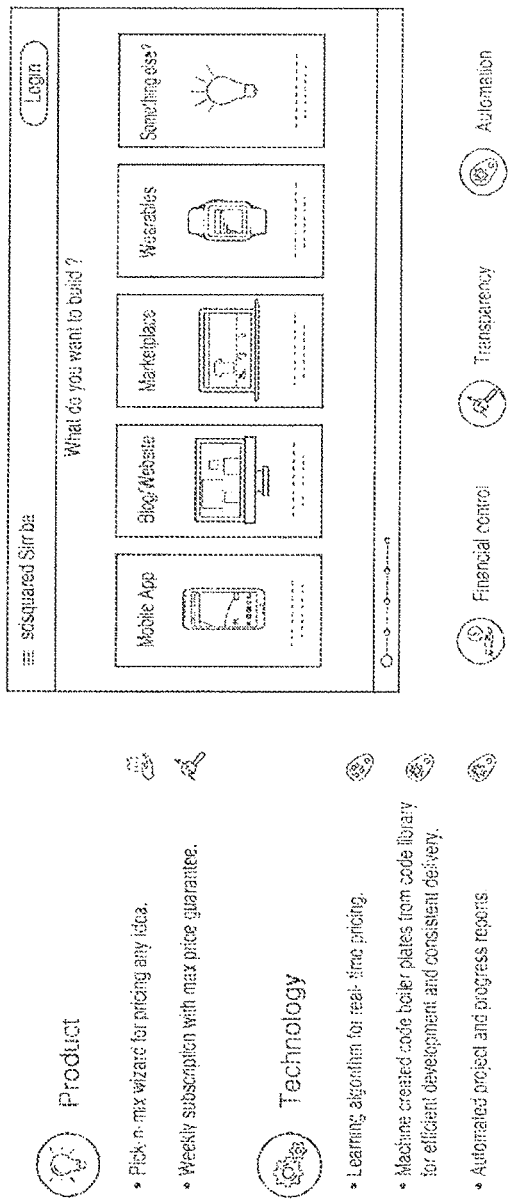
Figure 10:
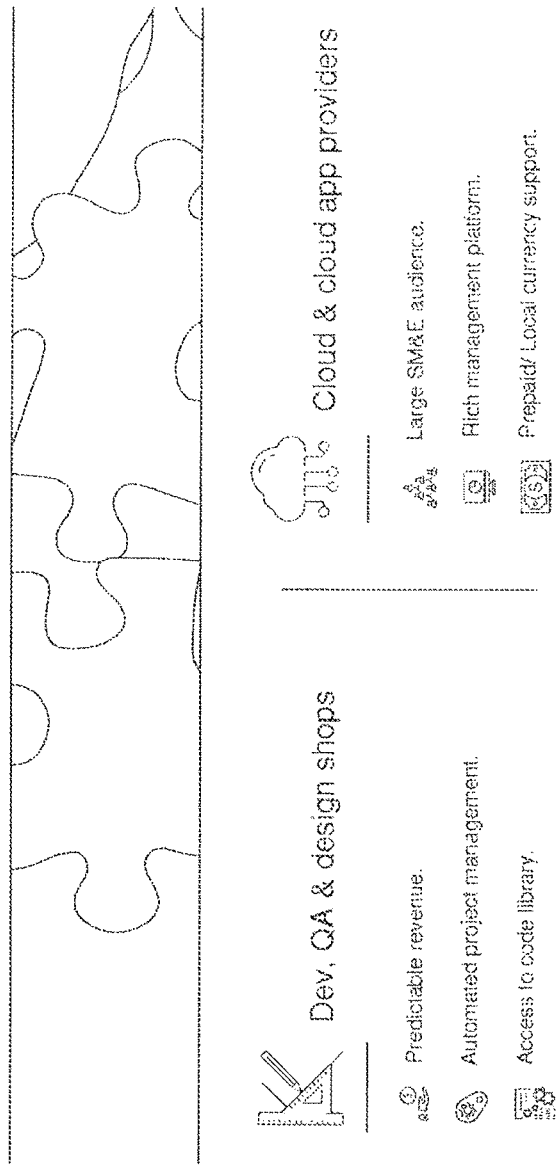
Figure 11:
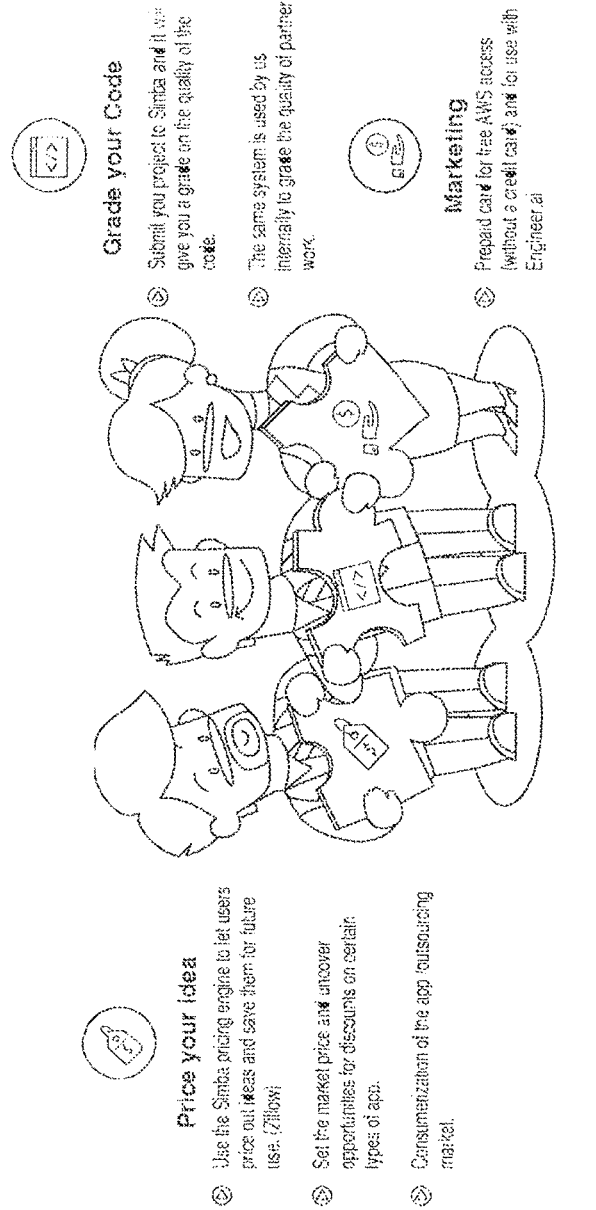
FIGS. 11-12 describe and illustrate aspects of how the user acquires access to embodiments and aspects of the value provided by embodiments of the systems and methods.
Figure 12:
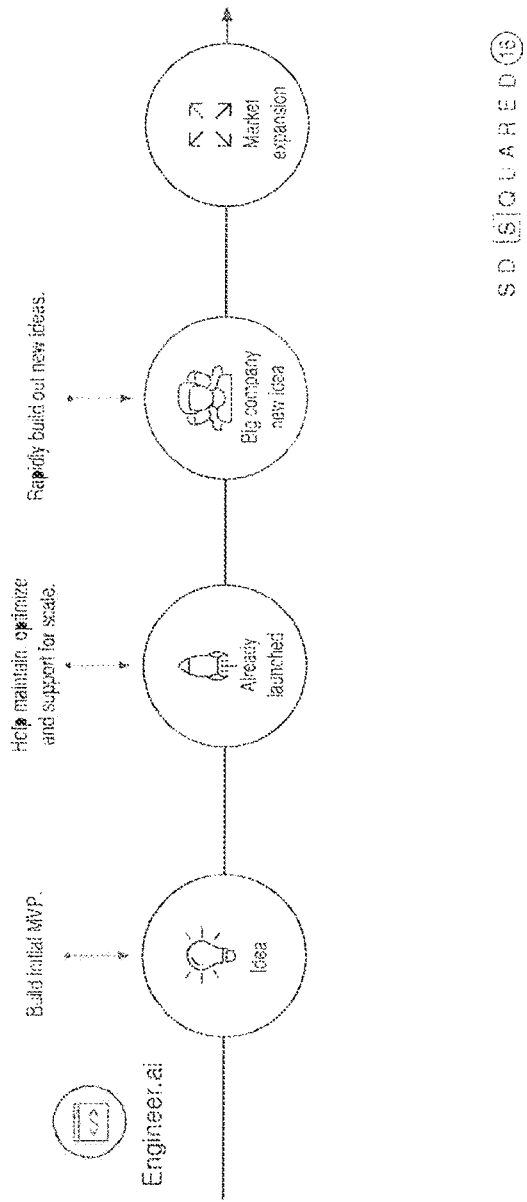
Figure 13:
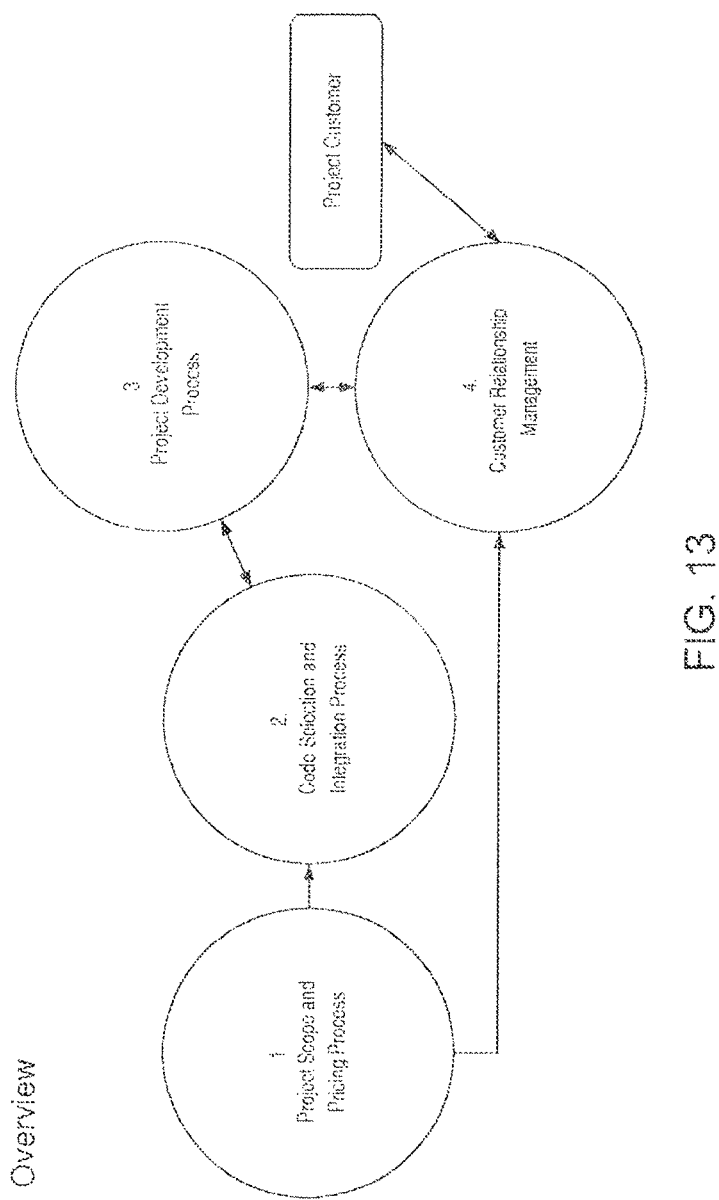
FIG. 13 is a block diagram illustrating an overview of an embodiment for creating software.
Figure 14:
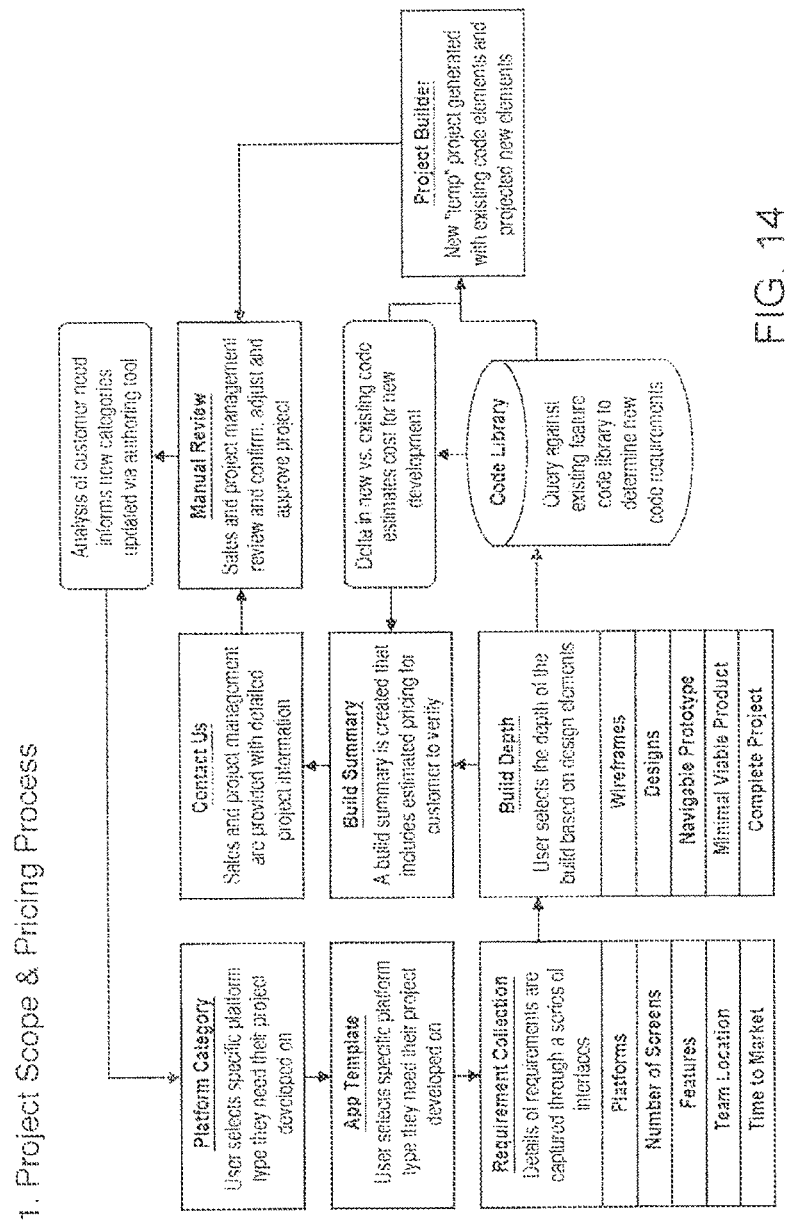
FIG. 14 is a block diagram illustrating a project scope and pricing process of an embodiment for creating software.
Figure 15:
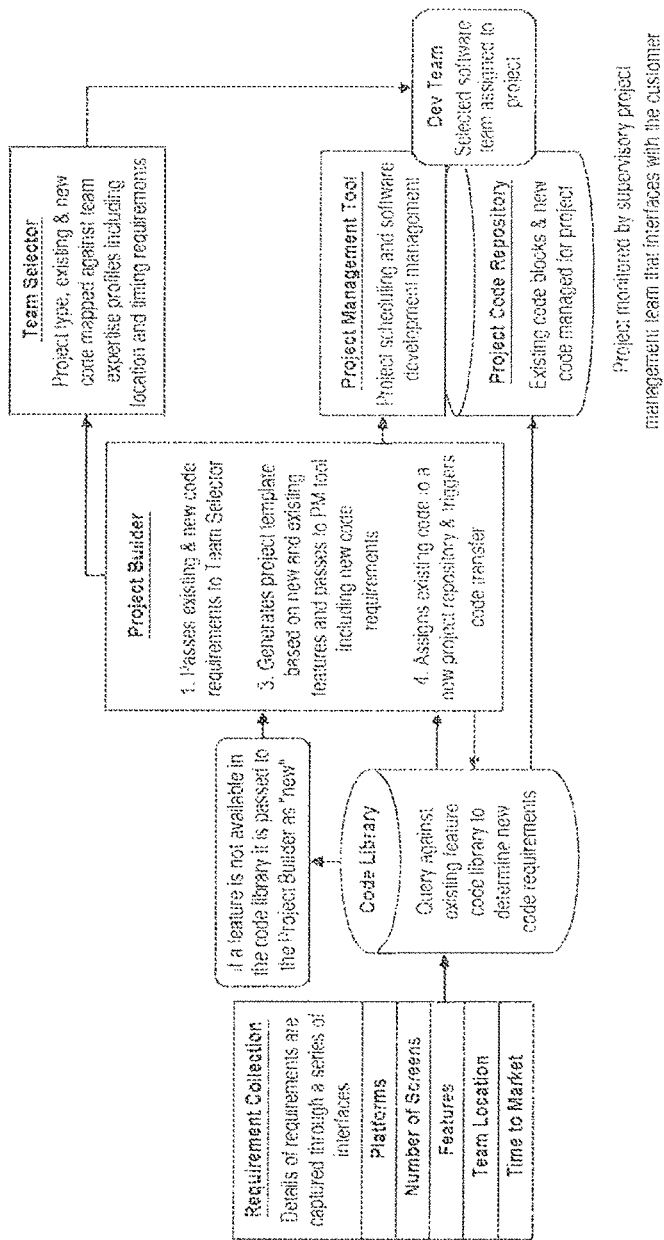
FIG. 15 is a block diagram illustrating a code selection and integration process of an embodiment for creating software.
Figure 16:
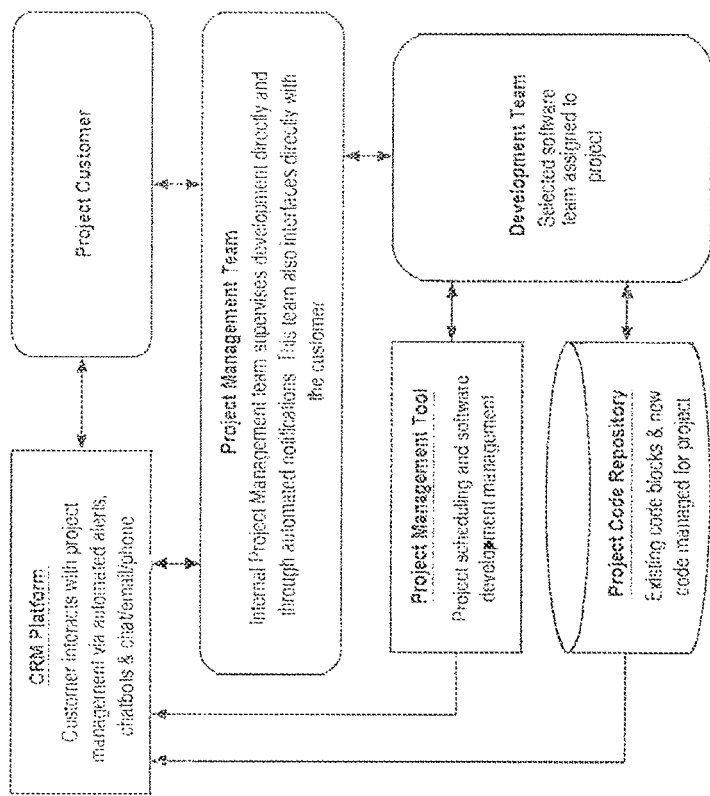
FIG. 16 is a block diagram illustrating a project development process of an embodiment for creating software.
Figure 17:
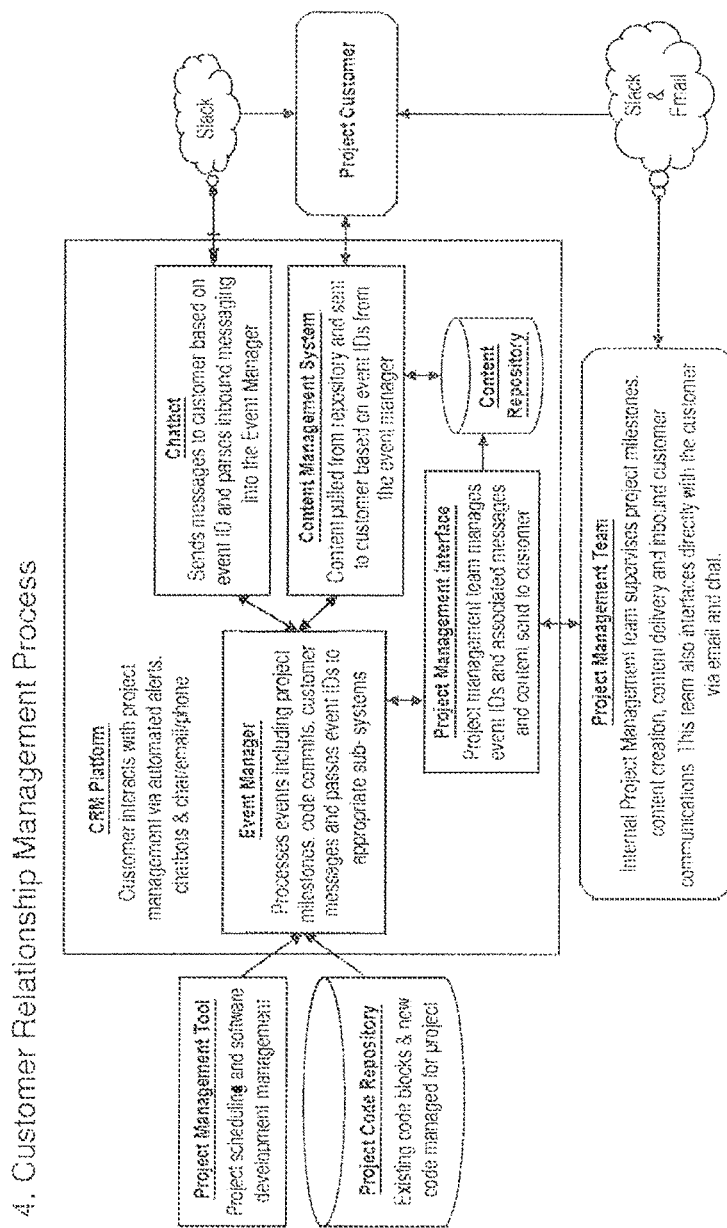
FIG. 17 is a block diagram illustrating a customer relationship and management process of an embodiment for creating software.

FIG. 4 is a diagram showing block diagrams of system architecture of an embodiment for creating software.

In an embodiment, a method for creating software is called "Engineer.ai."

Why was Engineer.ai created? Engineer.ai was created to allow for the building of digital products at least 30% faster and for 30% less than anyone else in the industry, all while guaranteeing top quality.

What is it and how does it work? Engineer.ai is an "as-a-service" platform for software outsourcing, turning App Development/Software Outsourcing into something as simple as a restaurant menu that you can pick a-la carte. This includes an On-Demand & Online Price Calculator for building any digital product from a Wearable to a Marketplace to an App with price guarantees, and intelligent automation/machine assistance that reduces the average cost and time of any project by at least 30%-40%. Engineer.ai offers a transparent fixed price upfront. No surprises and any amount over your fixed price is waived.

How does the service/product work? Engineer.ai provides an intuitive and easy-to-use wizard for pricing any idea in less than 60 seconds with pre-set options made available based on the project type. The fixed price you get is offered immediately and upfront. You don't need to wait or speak to a salesperson to know exactly what your project will cost and how long it will take to deliver.

How is my project managed? Engineer.ai provides weekly updates so you always know the exact status of your project. Engineer.ai practices gold standard for coding so quality is never sacrificed. Engineer.ai offers a weekly subscription and billing model so you are never locked in and can pause, speed up, or walk away at anytime.

Engineer.ai Benefits
1) Build your idea for 30% less and 30% faster than your competitors.
2) Use our easy-to-use wizard for pricing any idea in less than 60 seconds.
3) Get transparent and fixed pricing for your project upfront and instantaneously without speaking to a sales rep.
4) Have the confidence your project will be delivered on time and will not go over budget.
5) If you are not sure what you want, use our wizard to build out your idea by choosing from a bundle of pre-set options.

Engineer.ai Description

Engineer.ai uses machines to automate and institutionalize as much of the software outsourcing process as possible. Engineer.ai includes transparent pricing, standardized delivery, and a manufacturing-styled approach to development that reuses an estimated 50% of code and design that is often standardized and duplicated across many apps and digital platforms.

A key part of our business model is how Engineer.ai actually scales and builds. Engineer.ai scales by using 3rd party dev shops/contractors and having them deliver under the Engineer.ai brand, and Engineer.ai uses code libraries. Similarly Engineer.ai lets Software Companies get predictable revenue, a framework that lets them get paid and a way for them to access our rich code libraries & SIMBA Platform (Simple, Integrated, Machine-Based, Architecture Platform). Engineer.ai also scales by the institutionalization of the Engineer.ai code and development process.

SIMBA connects the entire product delivery process together. It integrates on-boarding, pricing, engineering and product/project management using machine-learning processing and A.I. ("artificial intelligence") to keep constant conversation with the customer. Aspects of SIMBA include:
  A "Pick-n-mix" wizard for pricing any idea.
  A weekly subscription with max price guarantee.
  A learning algorithm for real-time pricing.
  A machine-created templates from code library for efficient & consistent delivery.
  And an automated project and progress reports to ensure that customers have transparency in pricing, financial control, and automation
Engineer.ai is the first service to unify Development Shops around the world:
  First published pricing platform that lets your price an app or an idea within 30 seconds online.
  First process-driven and machine-led manufacturing approach for building software in a "just-in-time" model.
  First use of machine-learning and Artificial Intelligence in machines and BOTs (software applications that run automated tasks (scripts) over the Internet) to automate the product delivery process.
  For areas Engineer.ai feels need more "business interest," Engineer.ai may subsidize the development, such as efforts with content-led marketplaces; Engineer.ai can effectively invest in customers by simply offsetting some of its fees.

Role of SIMBA in Engineering.ai:
Automated Pricing
Machine-assisted product management
Code creation
Engineer.ai—Features
1) Project selector
   a) Category selection
      i) Current categories
      ii) Option for more categories
      iii) Metrics to track selection and % completion
   b) Template type
   c) Other project description (outside selector parameters)
   d) Platforms
   e) Feature preview
   f) Portfolio examples
   g) Team location
   h) Dev speed (time to market)
   i) Build fidelity
2) Pricing estimate
   a) Real time projected cost based on project guidelines created in the selector
3) Customer contact capture & confirmation
   a) Project review (can user adjust here?)
   b) Customer contact collected
   c) Saved confirmation of submission via email Engineer.ai—Additional Features
1) Project estimator additional features
   a) Wireframe database
   b) Intelligence re: additional categories & dataset
   c) Mobile & touch friendly
   d) Workflow for customer/sales interaction
   e) In an embodiment, the method makes a decision based on historical variance. For example, if there is some customization required for a particular type of app, and if the type of app shows a historical cost variation, the method adjusts the potential customization cost based on the historical variation.
2) Payment & contract execution
   a) Proposal automation
      i) Proposal based on integration (the degree and depth of integration)
   b) Billed deposit and weekly, monthly invoice
   c) Pay from invoice
3) Design
   a) Goal to assign to the right designer
   b) Preview based on component elements & wireframes
   c) Map to design library
   d) 2-3 week iteration with customer (details?)
4) Project team assignment
   a) Semi-automated
   b) Track team member status & availability projection
5) Component user story generation
   a) Board creation b) Database of tagged stories
c) Feature based story selection
6) Base code generation
   a) Code pods
   b) Feature based pod selection
7) Sprint estimator
   a) Feature/team/speed based estimation of completion
   b) Automated notifications of progress, potential deadline extensions, and sprint completions Engineer.ai—Partner Development Qualification Process
1) Sources
   a) Inbound
      i) Website
   b) Outbound
   c) Referral
2) Pre-qualification
   a) Minimum team requirements
   b) Ideal candidate profile—measure fill rate success/skills, experience, etc
   c) Team profiling tool
      i) Team members
      ii) Skills (dev lang, years experience, code committed)
      iii) Projects (associated projects)
3) Project review
   a) Minimum project examples—Live products ideal
   b) Customer testimonials
4) Code review
   a) Standardized code submission
   b) Submission, automated and manual review, and workflow process TABLE 1 gives a description of pages from a website employing embodiments of a method for creating software from library and custom components. In TABLE 1, a particular webpage is identified by the columns: ID, Title, and Labels. A Description column includes a description of the particular webpage and its function.

Figure 18:
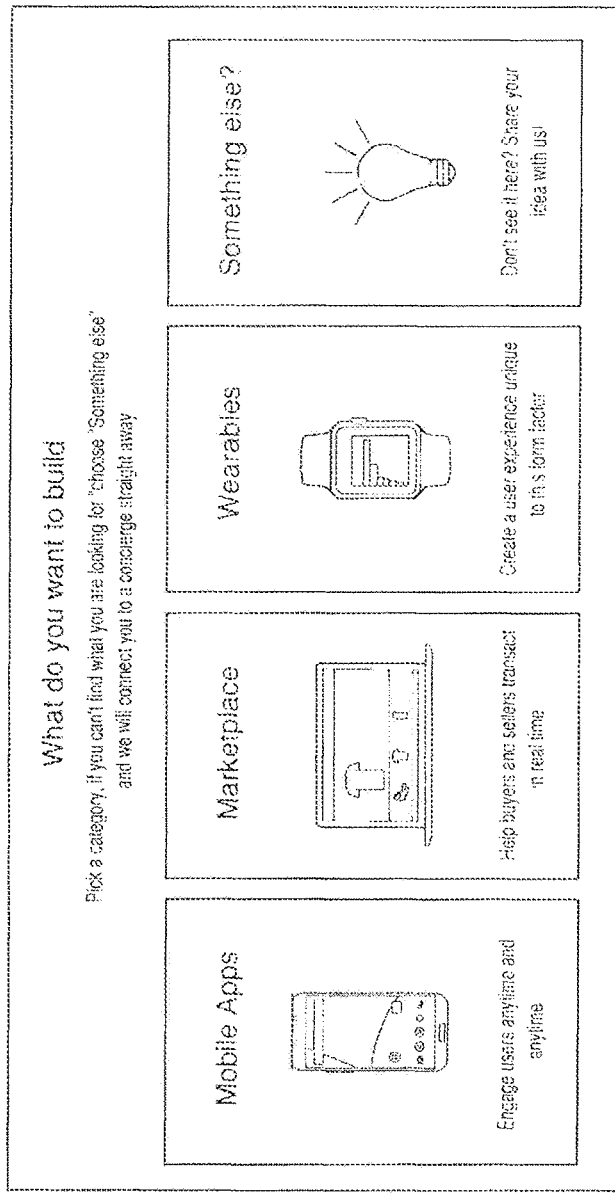
Figure 19:
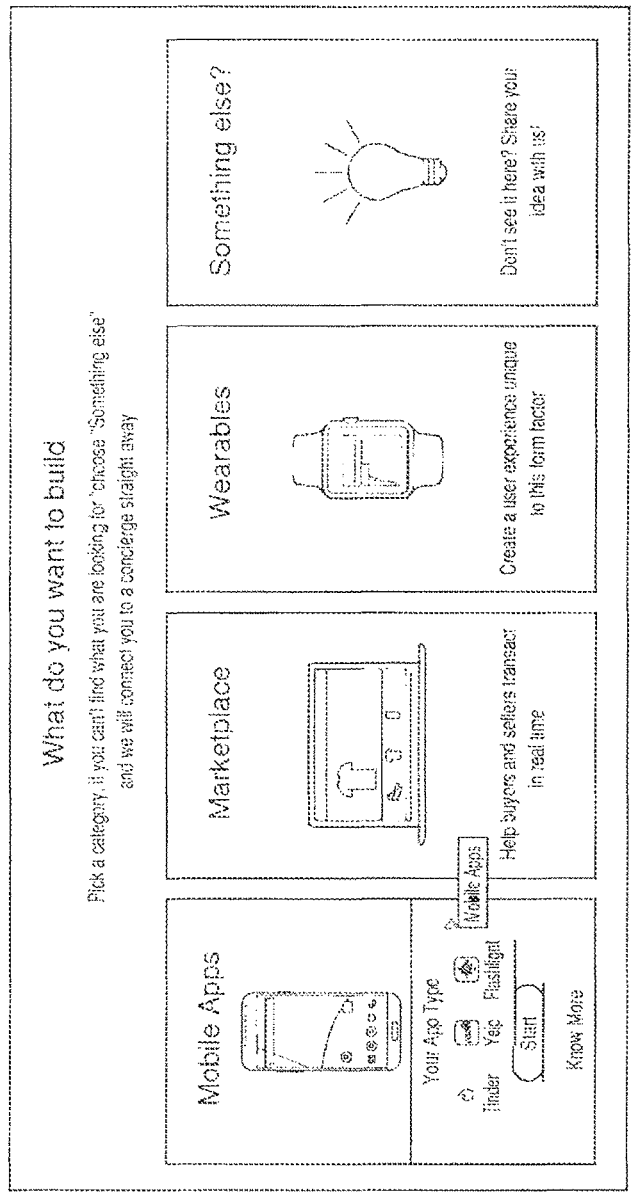
Figure 20:
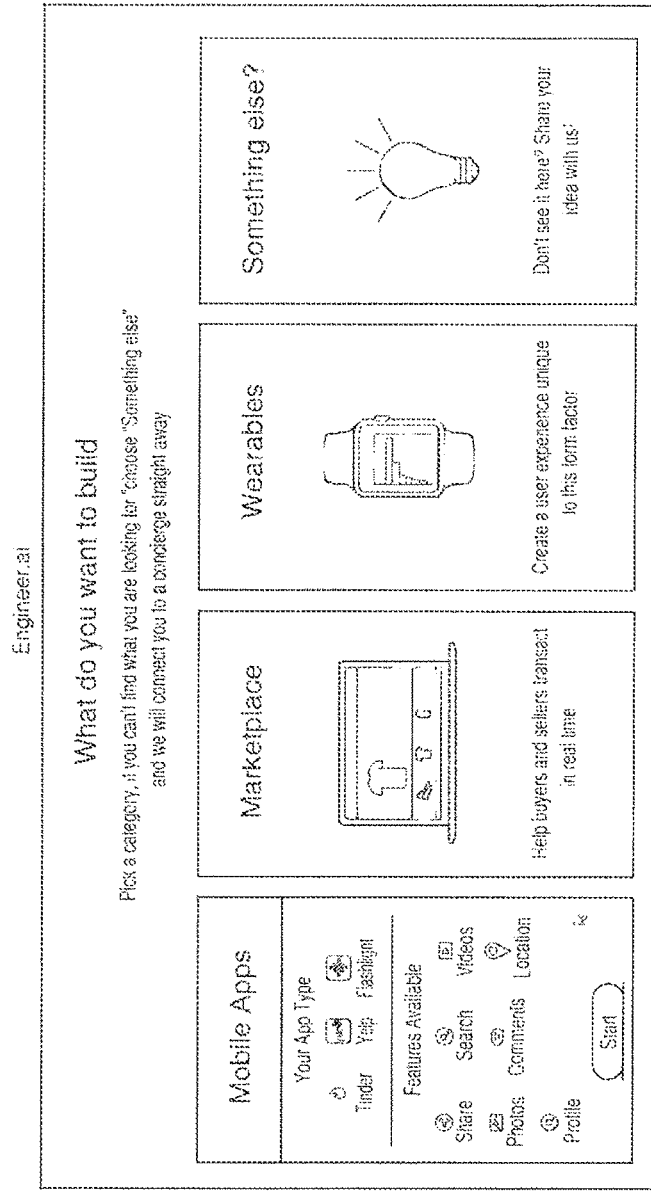
Figure 21:
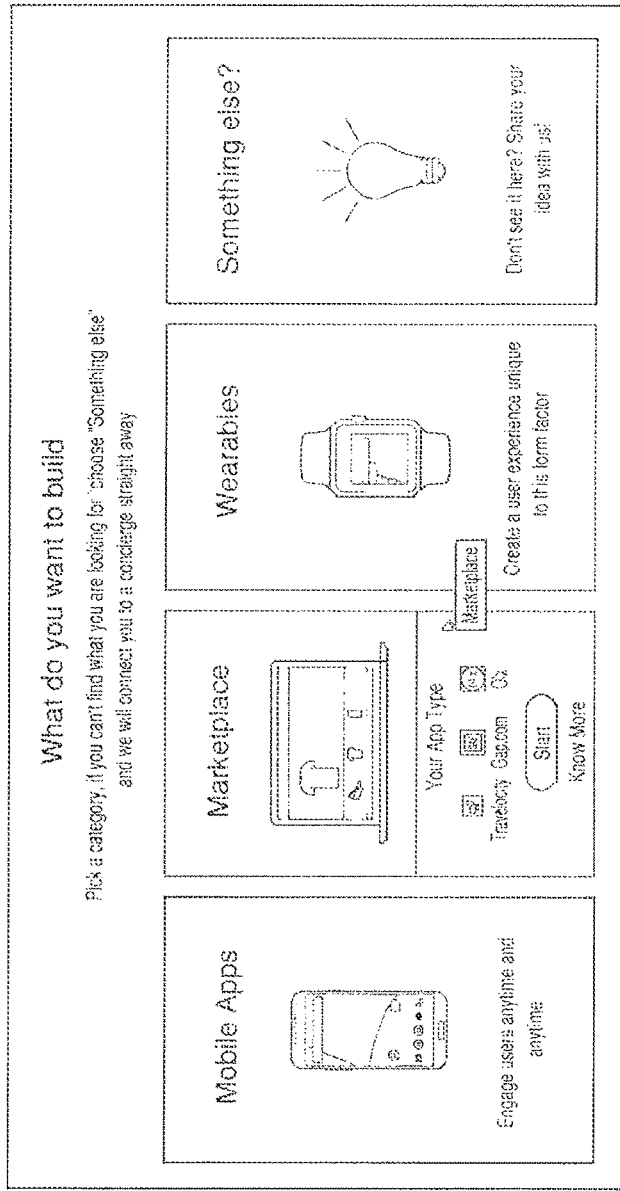
Figure 22:
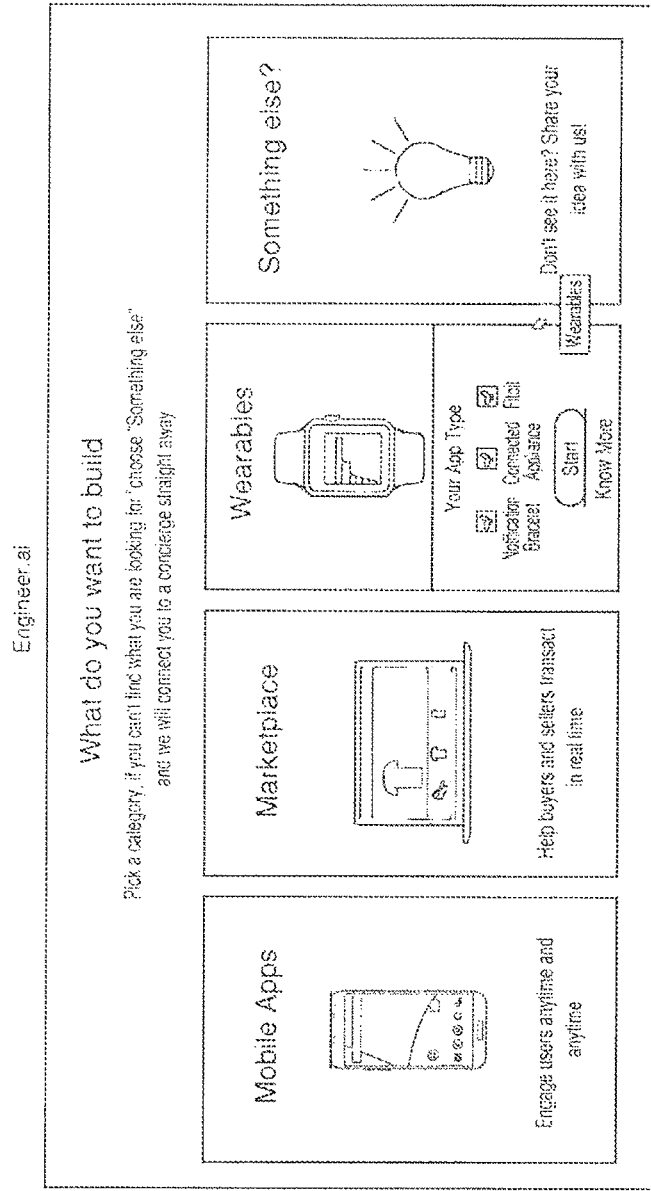
Figure 23:
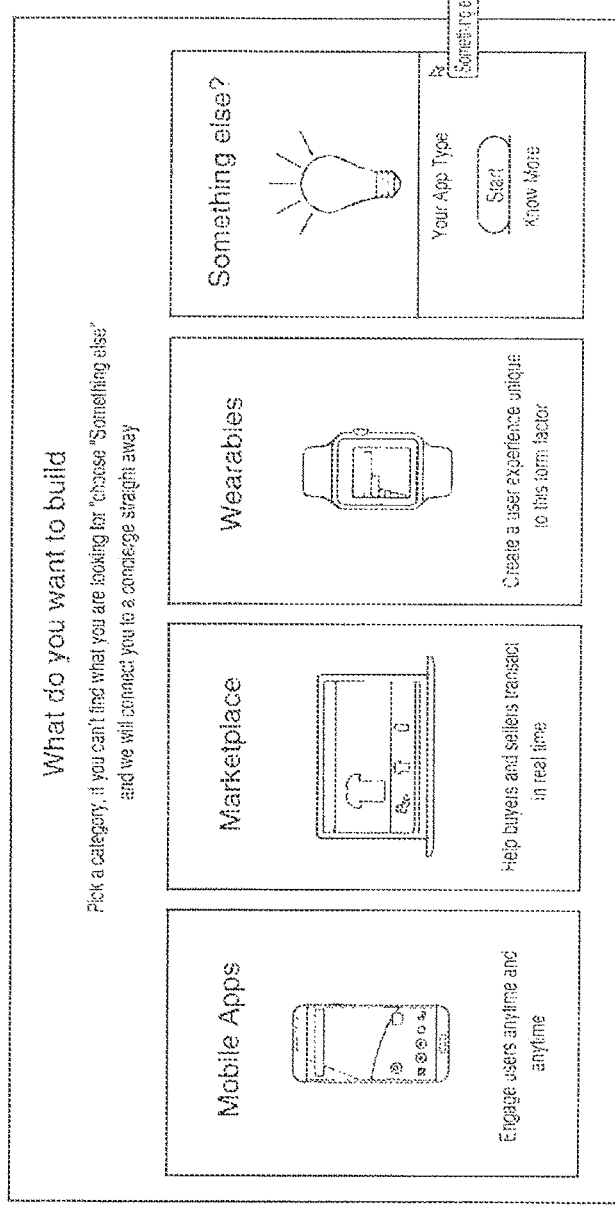
Figure 24:
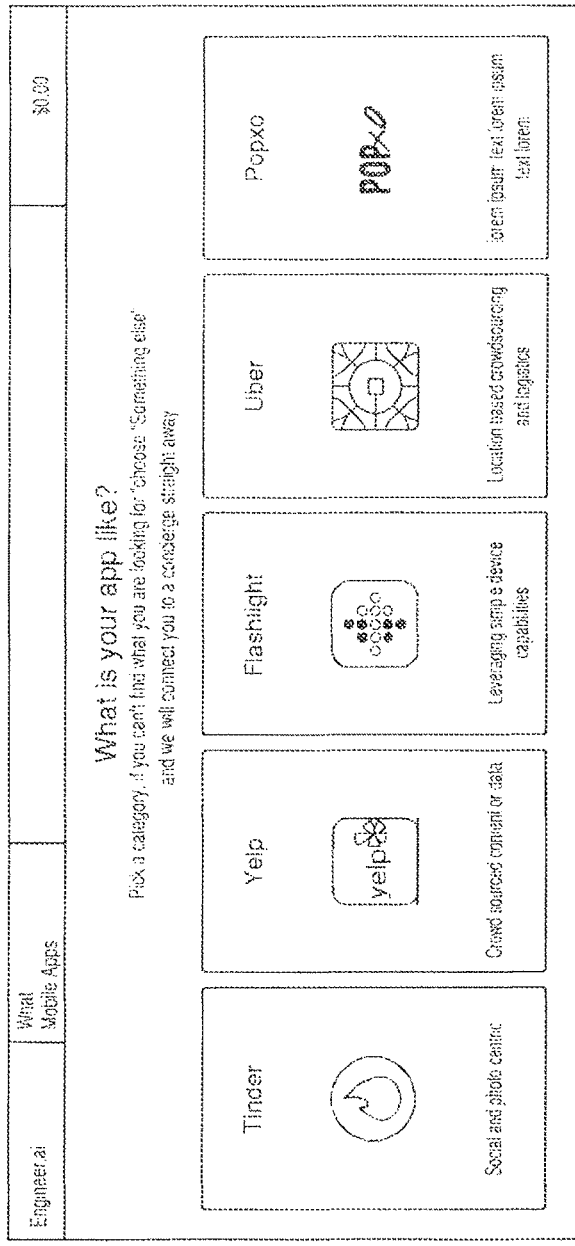
Figure 25:
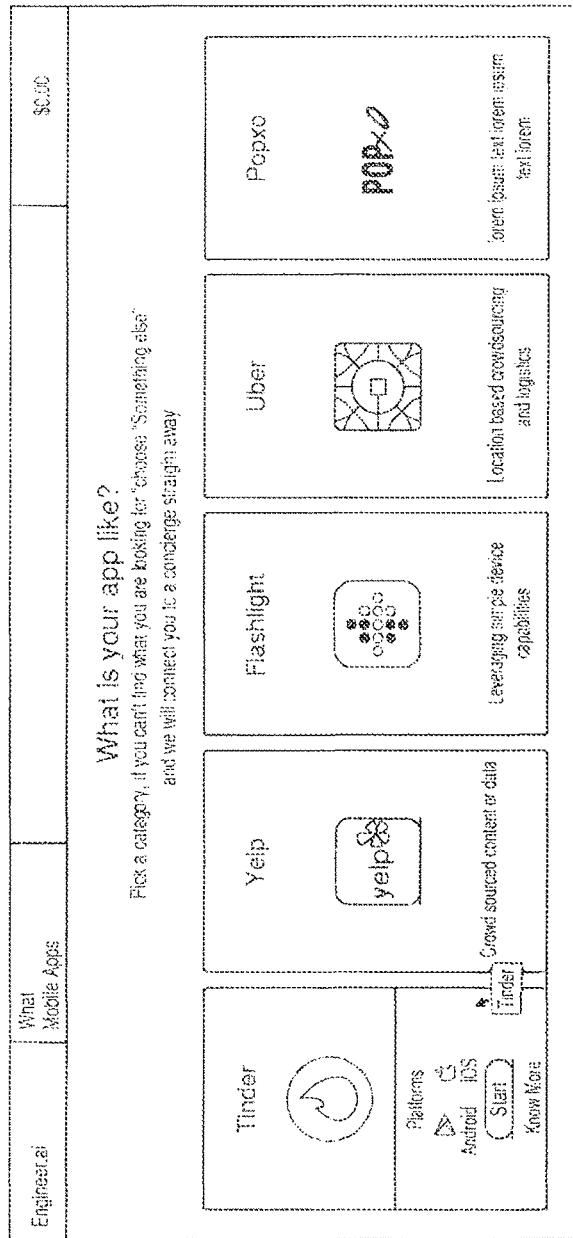

| ID | TITLE | LABELS | DESCRIPTION |
|---|---|---|---|
| 129382929 | Product Homepage/ Landing Page | homepage | As a user when I navigate to Engineer.ai's URL, I will be navigated to landing page of Engineer.ai.<br>The Landing page will present 5 Main Card options to choose from.<br>1. Mobile App<br>2. Blog/Website<br>3. Marketplace<br>4. Wearables<br>5. Others<br>Note: The entire text on cards like title, description etc. along with icons is not hardcoded and is available through backend. Please ignore text on all cards in the design references.<br>See, e.g., the screenshot on FIG. 18 for design reference. |
| 129383567 | Homepage \| Card Hover State | homepage | As a user, when I hover on the cards on the landing page, then the Main card will move up and an overlay card will reveal options related to the main card.<br>I should also see two buttons - Start and Know More.<br>Note: The entire text on cards like title, description etc. along with icons is not hardcoded and is available through backend. Please ignore text on all cards in the design references.<br>See, e.g., the screenshot on FIG. 19 for design reference. |
| 129446881 | Homepage \| Card Hover State \| Know More | homepage | As a user, when I click on *Know more* button after hovering on a card, there should be another overlay over the same card revealing the full feature set that are applicable for card being hovered upon.<br>The feature set list can be longer than the display area and thus needs to be horizontally scrollable.<br>A start button will also appear below the feature list. I can click on *Start* button and should be able to follow story #129446683<br>There will be another button under start by the name of * Portfolio Projects*. Clicking on it will work as described in story #129447399<br>Note: The entire text on cards like title, description etc. along with icons is not hardcoded and is available through backend. Please ignore text on all cards in the design references.<br>See, e.g., the screenshot on FIG. 20 for design reference. |
| 129440667 | Personalize Product \| Select Platform | personalize product | As a user, when I am navigated to this screen through the workflow defined in story #129521135, I should see the first section to select the platforms I need to support in my Product. This is the first step towards personalization of my product.<br>Below the applicable platforms list, I should be able to see the number of screens anticipated in my product.<br>A Next button appears below, clicking on which I should be able to follow story #129514959. This button gets enabled only when I have one or more |

Figure 30:
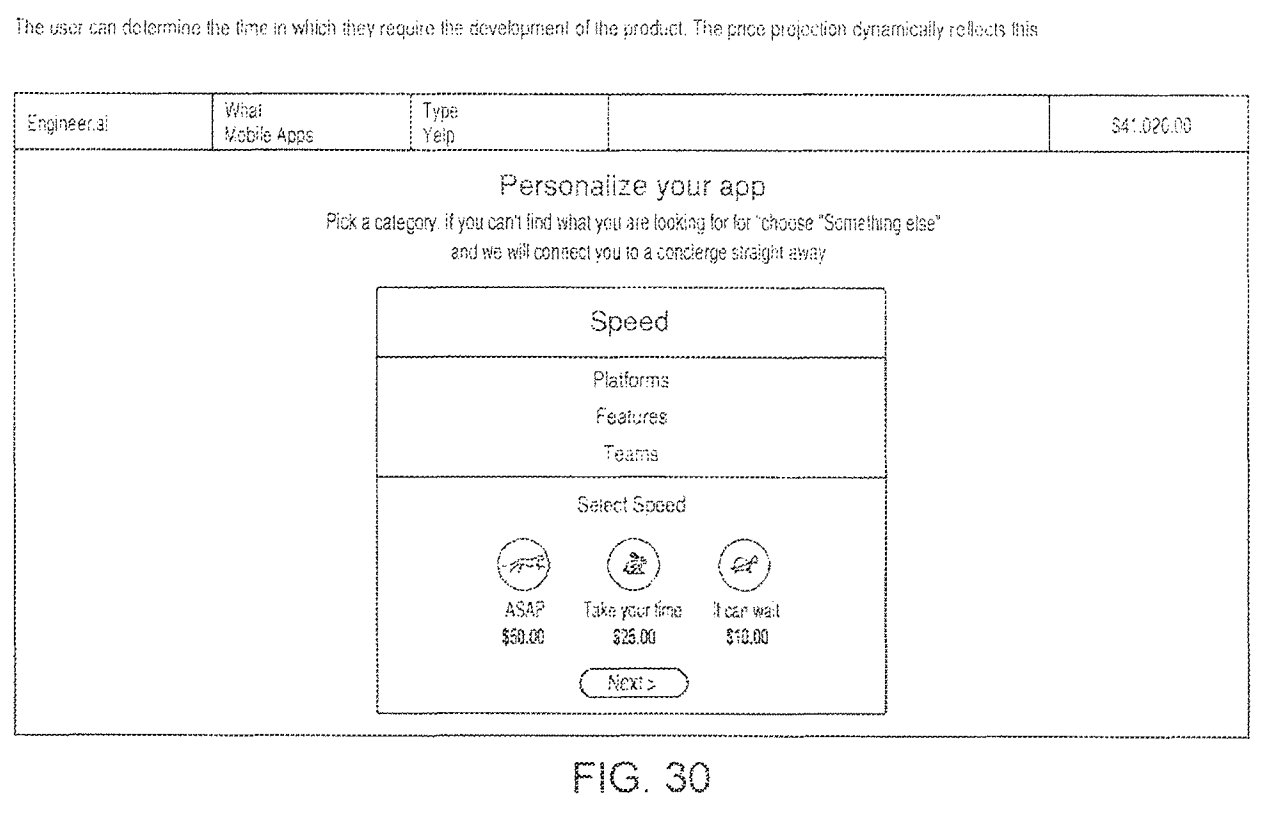
Figure 36:
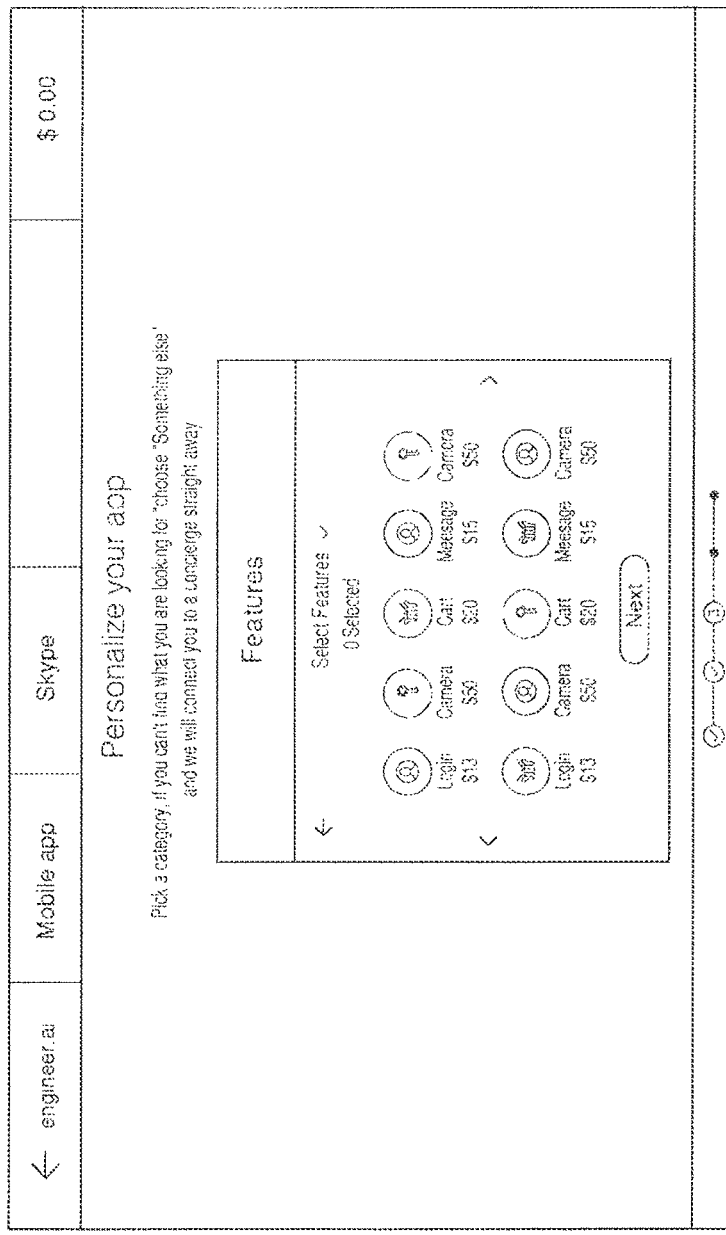

| ID | TITLE | LABELS | DESCRIPTION |
|---|---|---|---|
| | | | options from all required fields selected in this section.<br>Note: The entire text on cards like title, description etc. along with icons is not hardcoded and is available through backend. Please ignore text on all cards in the design references.<br>See, e.g., the screenshot on FIG. 27 for design reference. |
| 129515019 | Personalize Product \| Select Delivery Speed | personalize product | As a user, when I am navigated to this screen through the workflow defined in story #129514959 (on click on next), the third section overlay should come to top. This will allow me to select the team I want to use to develop my product and is the third step towards personalization of my product.<br>A back button will appear below to the header clicking on which I will be navigated to Select Features story (#129514959)<br>A Next button appears below, clicking on which I should be able to follow story #129515169. This button gets enabled only when I have one or more options from all required fields selected in this section.<br>Note: The entire text on cards like title, description etc. along with icons is not hardcoded and is available through backend. Please ignore text on all cards in the design references.<br>See, e.g., the screenshot on FIG. 28 for design reference. |
| 129515169 | Personalize Product \| Select Delivery Speed | personalize product | As a user, when I am navigated to this screen through the workflow defined in story #129515019 (on click on next), the third section overlay should come to top. This will allow me to select the speed of delivery for my product and is the fourth step towards personalization of my product.<br>A back button will appear below to the header clicking on which I will be navigated to Select Features story (#129515019)<br>A Next button appears below, clicking on which I should be able to follow story #129522065. This button gets enabled only when I have one or more options from all required fields selected in this section.<br>Note: The entire text on cards like title, description etc. along with icons is not hardcoded and is available through backend. Please ignore text on all cards in the design references.<br>See, e.g., the screenshot on FIG. 30 for design reference. |
| 129514959 | Personalize Product \| Select Features | personalize product | As a user, when I am navigated to this screen through the workflow defined in story #129440667 (on click on next), the second section overlay should come to top. This will allow me to select the features I need to include in my Product and is the second step towards personalization of my product.<br>A Back Button will appear below to the header clicking on which I will be navigated to Select Platform & Pages story (#129440667)<br>A Next button appears below, clicking on which I should be able to follow story #129515019. This button gets enabled only when I have one or more options from all required fields selected in this section.<br>Note: The entire text on cards like title, description etc. along with icons is not hardcoded and is available through backend. Please ignore text on all cards in the design references.<br>See, e.g., the screenshot on FIG. 36 for design reference. |
| 129446683 | Product Type Landing Page (Start from any card on Homepage) | homepage, product type | As a user, when I click on *Start* button from hover state or additional card overlays, I should be navigated to a separate page which will show cards based on the card selected on homepage.<br>Additionally, if I click on header section of this card, the same workflow should be followed.<br>Note: The entire text on cards like title, description etc. along with icons is not hardcoded and is available through backend. Please |

-continued

Figure 26:
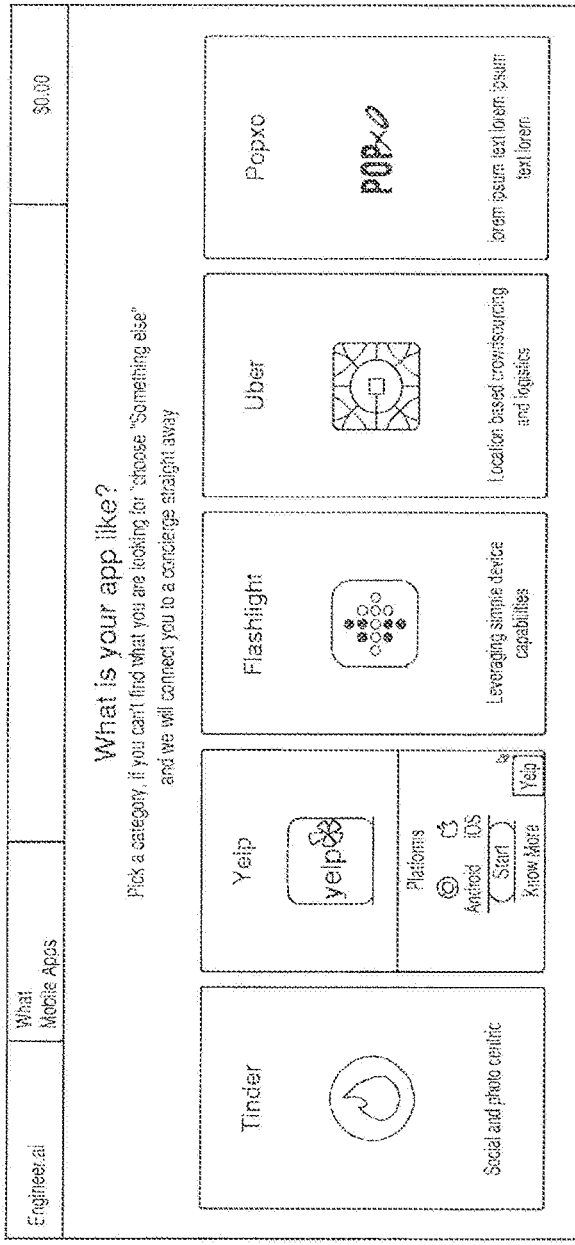
Figure 29:
Figure 32:
Figure 33:
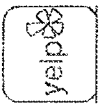
Figure 35:
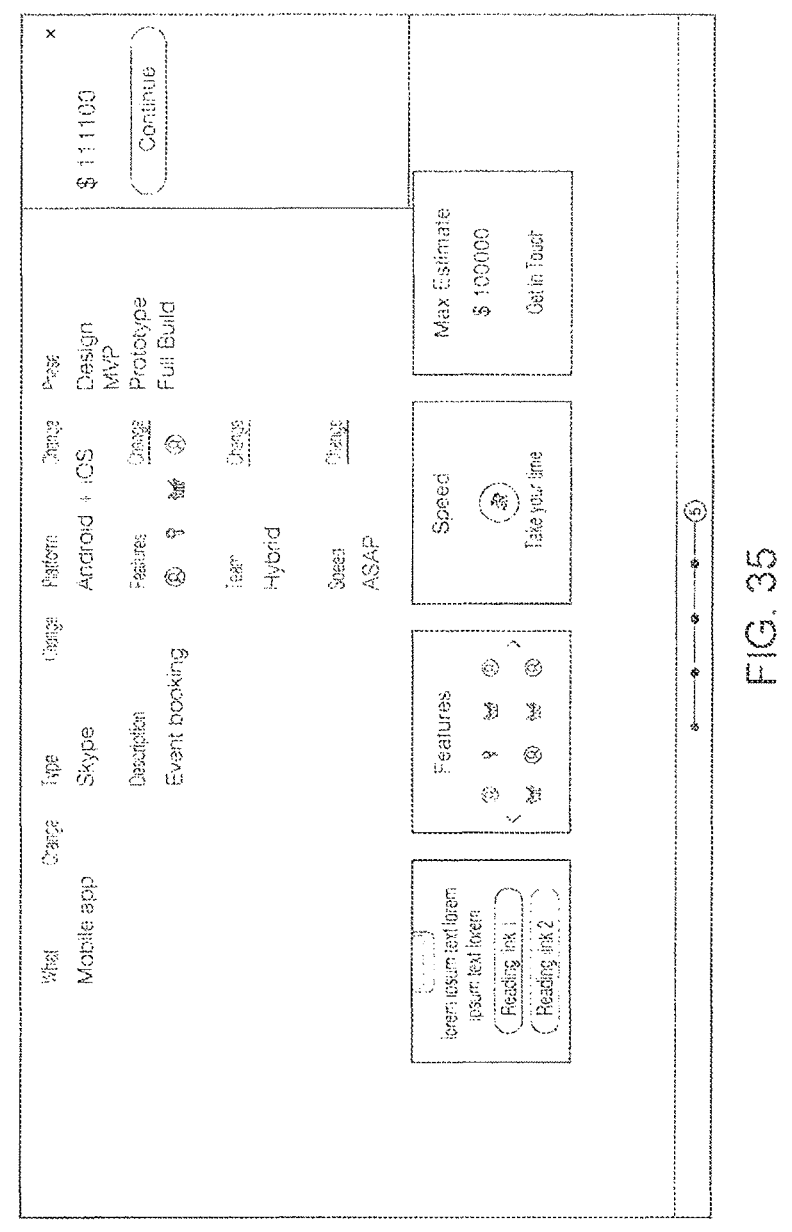

| ID | TITLE | LABELS | DESCRIPTION |
|---|---|---|---|
| | | | ignore text on all cards in the design references. See, e.g., the screenshot on FIG. 35 for design reference. |
| 129514073 | Product Type Page \| Card Hover State | product type | As a user, when I hover on a card in Product Type page, the card should show the list of platforms that are applicable for that product type.<br>A *Know more* button will also appear below the applicable platforms list. I can click on this button and should be able to follow story #129514203<br>On clicking the header of this card, I should be able to follow story #129514387<br>Note: The entire text on cards like title, description etc. along with icons is not hardcoded and is available through backend. Please ignore text on all cards in the design references.<br>See, e.g., the screenshot on FIG. 26 for design reference. |
| 129522743 | Personalize Product \| Your Build Card | personalize product | As a user, when I am navigated to this screen through the workflow defined in story #129522065 (on click on next), the build card should appear. This screen shows your selections through 4 cards as showcased in the design reference.<br>It should display the following 4 cards in the given order:<br>* Product Type with description<br>* Platform, Screens and Features list<br>* Team and Speed<br>* Development Phases and Estimate<br>A Get in Touch button appears inside the 4th card, clicking on which I should be able to follow story #129522917.<br>Note: The entire text on cards like title, description etc. along with icons is not hardcoded and is available through backend, unless stated otherwise. Please ignore text on all cards in the design references.<br>See, e.g., the screenshot on FIG. 33 for design reference. |
| 129522065 | Personalize Product \| Select Project Phases | personalize product | As a user, when I am navigated to this screen through the workflow defined in story #129515169 (on click on next), the phase selection screen should appear. It is the final step towards personalization of my product and product development lifecycle.<br>It should display the following 4 phases:<br>* Design<br>* Prototype<br>* MVP<br>* Full Build<br>By default all the 4 phases will be selected. As a user, I should also be able to unselect the selected card(s) as many times and vice-versa.<br>The estimate in header should update instantly based on the selections I am making.<br>A Next button appears below, clicking on which I should be able to follow story #129522743. This button gets enabled only when I have one or more options from all required fields selected in this section.<br>Note: The entire text on cards like title, description etc. along with icons is not hardcoded and is available through backend, unless stated otherwise. Please ignore text on all cards in the design references.<br>See, e.g., the screenshot on FIG. 32 for design reference. |
| 129514203 | Product Type Page \| Card Hover State \| Know More | product type | As a user, when I click on *Next* button on hovered card in Products page, I should be able to see the features I can request for. The card overlay that opened in previous view moves a bit up to accommodate the list.<br>If the list requires more space than available in the display area, the list should be horizontally paginated.<br>A *Next* button will also appear below the applicable features list. I can click on this button and should be able to follow story<br>Note: The entire text on cards like title, description etc. along with icons is **not |

-continued

Figure 34:

| ID | TITLE | LABELS | DESCRIPTION |
|---|---|---|---|
| | | | hardcoded** and is available through backend. Please ignore text on all cards in the design references. See, e.g., the screenshot on FIG. 20 for design reference. |
| 129757983 | Add in pricing component | | Depending on what the user selects, the price should constantly be updating in the top-right section of the navbar |
| 129521135 | Create the Personalize Product Page | personalize product | As a user, when I am navigated to this screen through the workflow defined in story #129514387, I should see a card that has 4 dynamic sections stacked over one another. These sections (in defined order) are<br>* Select Platforms *(Hard Coded Label)*<br>* Select Features *(Hard Coded Label)*<br>* Select Team *(Hard Coded Label)*<br>* Select Speed *(Hard Coded Label)*<br>Initially, only the first section will be enabled and rest will be disabled. As and when I keep selecting options in each section, the next section in stack gets enabled. I can also navigate directly between all the enabled sections directly by clicking them. The selected sections comes on top while others are visible in the background.<br>For linear navigation between enabled sections, I should also be able to use the Back and Next button in each sections. The first section should not have a back button.<br>Note: The most of the text in sections like title, description etc. along with icons is not hardcoded and is available through backend; unless stated otherwise.<br>See, e.g., the screenshot on FIG. 27. |
| 129522917 | Personalize Product \| Get in Touch Screen | personalize product | As a user, when I am navigated to this screen through the workflow defined in story #129522743 (on click on "Get in Touch" button), the Get in Touch screen should appear. This screen should allow me to enter information in following fields:<br>* Project Name (100 Characters)<br>* Project Description (150 Characters)<br>* My email ID (75 Characters)<br>* My Name (50 Characters)<br>Below these fields, there should be a checkbox asking me to confirm that I agree to *Terms & Conditions* and *Privacy Policy*<br>I can also request for a *"Non Disclosure Agreement"* through another link below the above checkbox.<br>Lastly, I should be able to save the details and allow the team to connect with me. I should now be navigated to next screen which follows story #129523531.<br>See, e.g., the screenshot on FIG. 34 for design reference. |
| 129525811 | Show and update Header | | As a user I would like to see a dynamic header in the application. This header is visible when I click on Start on any of the main cards on the home screen.<br>The header has 5 sections (Collapsed form)<br>The header has 5 sections (Expanded form)<br>* Product Type<br>* Product Sub Type & Its description<br>* Platform, Features, Team and Speed<br>* Phase<br>* Estimate<br>Each section/sub-section will be added to header as and when user navigates to these pages/sections and makes necessary selections on screen.<br>Any update in these sections also instantly update the header with new information.<br>I can also click on Header to see the expanded view. Please see the below design for reference for collapsed view<br>See, e.g., the screenshot on FIG. 35 for design reference. |
| 129514387 | Product Type Page \| Add product description | product type | As a user, when I click on *Next* button on hovered card in Products page, an overlay will stack over existing overlays and allow me to add a description about the kind of product that I want to build. The description cannot be longer than 50 characters. |

Figure 37:
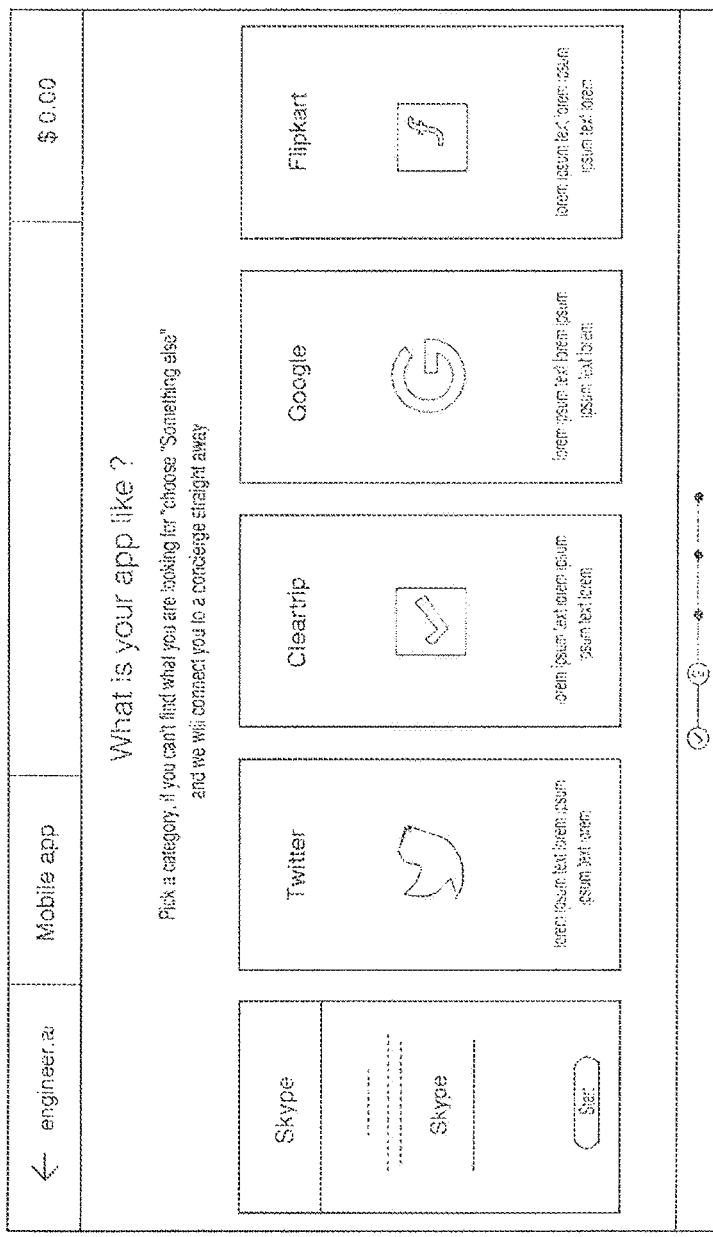
Figure 43:
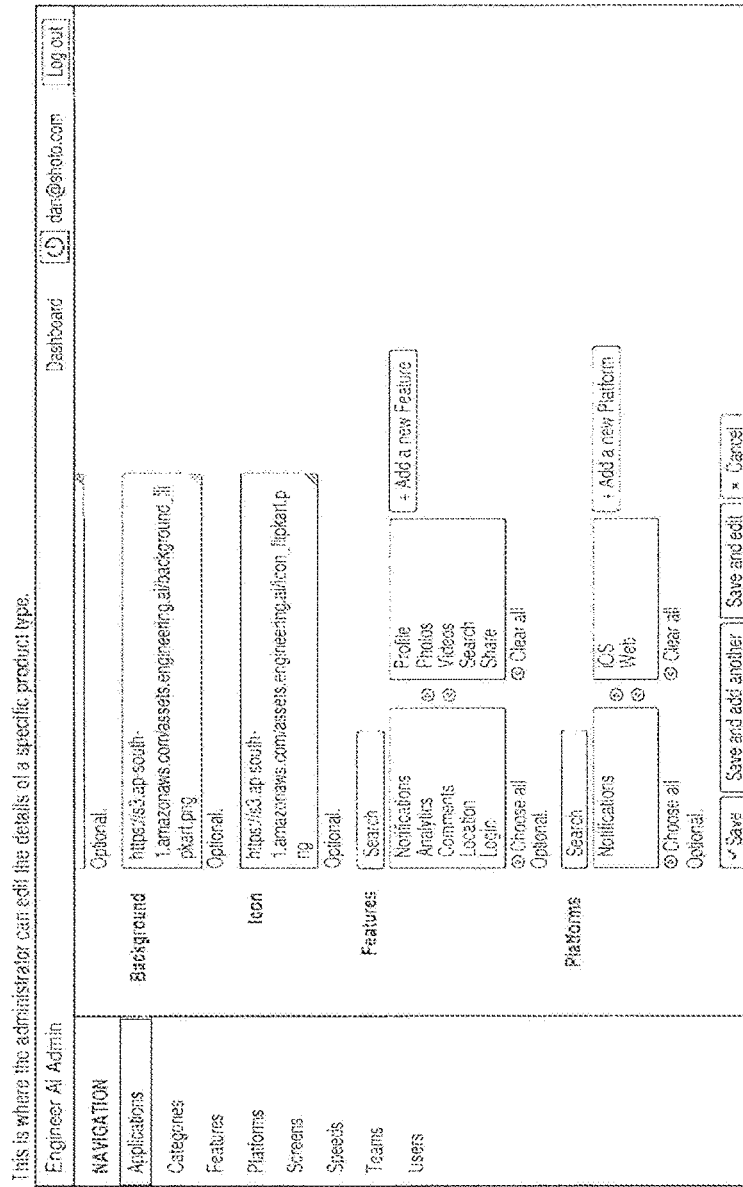

| ID | TITLE | LABELS | DESCRIPTION |
|---|---|---|---|
| | | | Alternately, I can reach here by clicking the card header on *Product Types* page at any point of time. A *Start* button appear below the text field. I can click on this button and should be able to follow story #129440667<br>Note: The entire text on cards like title, description etc. along with icons is not hardcoded and is available through backend. Please ignore text on all cards in the design references.<br>See, e.g., the screenshot on FIG. 37 for design reference. |
| 129523531 | Create the Concierge page | personalize product | As a user, when I am navigated to this screen through the workflow defined in story #129522917 (on click on "Get in Touch" button), the Concierge screen should appear.<br>Here, I should be able to post my queries and add attachments. Attachment types TBD.<br>Lastly, I should be able to start an estimation for a new build which redirects me to homepage. |
| 129447399 | Homepage \| Card Hover State \| Know More \| Portfolio | homepage, skip | As a user, when I click on * Portfolio Projects* button in know more section of a card on Home page, a new overlay will appear as showcased in the design reference.<br>It should show a list of 4 customers and a few testimonials. The testimonials should be horizontally scrollable.<br>A start button will also appear below the feature list. I can click on *Start* button and should be able to follow story #129446683<br>Note: The entire text on cards like title, description etc. along with icons is not hardcoded and is available through backend. Please ignore text on all cards in the design references. |

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment.

Systems and methods are described for creating software from library and custom components. In a method for creating software, a server running a software creating component may receive input from a customer, where the input describes at least one aspect of a software program. Based on the input, the software creating component may determine existing code components that may be used to create the software program, where the existing code components are stored in a code library accessible by the software creating component. Based on the user input and based on the existing code components that may be used to create the software program, the software creating component may determine new code components that must be developed for the software program. And, based on the existing code components that may be used and based on the new code components that must be developed, the software creating component may provide, to the user, a cost estimate for the software program.

Different embodiments may provide variations on the basic principles outlined above. In an embodiment, the method may further comprise adjusting the cost estimate based on the at least one aspect of the software program. In an embodiment, the at least one aspect of the software program may include at least one of: a platform category, an application template, a requirement collection, a platform, a number of screens, a feature, a team location, a time to market, and a build depth. In an embodiment, the build depth may include: a wireframe, a design, a navigable prototype, a minimal viable product, or a complete project. In an embodiment, the method may further comprise: sending, by the software creating program, a set of existing code requirement and a set of new code requirements to a team selector; and generating, by the software creating program, a project template based on the existing code components that may be used and based on the new code components that must be developed. In an embodiment, the method may further comprise: generating, by the software creating program, a project schedule based at least in part on the project template, the project schedule including events related to the creation of the software program; and managing, by the software creating program, the events related to the creation of the software program. In an embodiment, the events related to the creation of the software program may include at least one of: a project milestone; a code commit; and a customer message. In an embodiment, the method may further comprise: passing, by the software creating program, at least one event ID to a communication program; and sending, by the communication program, a message to the customer based on the event ID. And in an embodiment, the method may further comprise: receiving, by a communication program, a message from the customer; and parsing, by the communication program, the received message into the software creating program.

What is claimed is:

1. An integrated, machine-based architecture, software development system that connects a plurality of custom software development processes together comprising:
a computer configured to:
display webpages in which a series of menus assist a user in selecting a set of features to design a custom software application;
query against an existing feature code library to determine new code components required for the custom software application;
implement a project builder that generates a new project with existing code components from an existing feature code library and the new code components;
implement a price estimation process that generates and updates a price based on the selected features, the existing code components, and the new code components; and is configured to adjust the price using a price variance based on historical cost variation for customization required by the custom software application;
display the price to the user during a course of selecting features; and
display a build card comprising a summary of the user's interactive selection and the price, wherein the set of features comprise at least one of: a platform category, an application template, a requirement collection, a platform, a number of screens, a feature, a team location, a time to market, and a build depth, and
wherein the build depth comprises at least one of a wireframe, a design, a navigable prototype, a minimal viable product, and a complete project.

2. The system of claim 1 wherein the system is configured to allow users to interact with webpages to design the custom software application by being configured to display an interactive web page that presents a group of different types of software applications to select from to be a base for the custom software application.

3. The system of claim 2 wherein the system is configured to display a group of different types of software applications comprising a social and photo centric type, a crowd sourced content type, leveraging simple device capabilities type, or location based type.

4. The system of claim 2 wherein the system is configured to allow the user to select the one or more types of operating system for which the customer software application is developed.

5. The system of claim 1 wherein the system is configured to machine-assist the user to design the customer software application by displaying a series of interactive menu options from which the user selects an application type, operating systems, build depth, and other customizations.

6. The system of claim 1 wherein the system is configured to allow users to interact with webpages to design a custom software application by being configured to display an interactive web page that presents a group of different build depth to select from the development of the custom software application.

7. The system of claim 6 wherein the system is configured to allow the user to present an interactive webpage that display options for build depth comprising, wireframe depth, clickable user demo depth, core feature to beta test depth, and complete app for launch depth.

8. The system of claim 1 wherein the system is configured to automatically generate the price based on querying the code repository based on the build card.

9. An integrated, machine-based architecture, software development system that connects a plurality of custom software development processes together comprising:
a computer configured to:
display webpages in which a series of menus assist a user in selecting a set of features to design a custom software application;
query against an existing feature code library to determine new code components required for the custom software application;
implement a project builder that generates a new project with existing code components from an existing feature code library and the new code components;
trigger a transfer of code from the existing feature code library to a new project repository for the new custom software application; and
implement a price estimation process that generates and updates a price based on the selected features, the existing code components, and the new code components; and is configured to adjust the price using a price variance based on historical cost variation for customization required by the custom software application;
display the price to the user during a course of selecting features; and
display a build card comprising a summary of the user's interactive selection and the price, wherein the set of features comprise at least one of: a platform category, an application template, a requirement collection, a platform, a number of screens, a feature, a team location, a time to market, and a build depth, and
wherein the build depth comprises at least one of a wireframe, a design, a navigable prototype, a minimal viable product, and a complete project.

10. The system of claim 9 wherein the system is configured to allow users to interact with webpages to design the custom software application by being configured to display an interactive web page that presents a group of different types of software applications to select from to be a base for the custom software application.

11. The system of claim 10 wherein the system is configured to display a group of different types of software applications comprising a social and photo centric type, crowd sourced content type, leveraging simple device capabilities type, or location based type.

12. The system of claim 10 wherein the system is configured to allows the user to select the one or more types of operating system for which the customer software application is developed.

13. The system of claim 9 wherein the system is configured to machine-assist the user to design the customer software application by displaying a series of interactive menu options from which the user selects an application type, operating systems, build depth, and other customizations.

14. The system of claim 9 wherein the system is configured to allow users to interact with webpages to design a custom software application by being configured to display an interactive web page that presents a group of different build depth to select from the development of the custom software application.

15. The system of claim 14 wherein the system is configured to allow the user to present an interactive webpage that display options for build depth comprising, wireframe depth, clickable user demo depth, core feature to beta test depth, and complete app for launch depth.

16. An integrated, machine-based architecture, software development system that connects a plurality of custom software development processes together comprising:

a computer configured to:

display webpages in which a series of menus assist a user in selecting a set of features to design a custom software application, wherein the webpage permits the user to select a type of sample application and related features associated with the sample application;

query against an existing feature code library to determine new code components required for the custom software application;

implement a project builder that generates a new project with existing code components from an existing feature code library and the new code components;

trigger a transfer of code from the existing feature code library to a new project repository for the new custom software application; and implement a price estimation process that generates and updates a price based on the selected features, the existing code components, and the new code components; and is configured to adjust the price using a price variance based on historical cost variation for customization required by the custom software application;

display the price to the user during a course of selecting features; and display a build card comprising a summary of the user's interactive selection and the price, wherein the set of features comprise at least one of: a platform category, an application template, a requirement collection, a platform, a number of screens, a feature, a team location, a time to market, and a build depth, and wherein the build depth comprises at least one of a wireframe, a design, a navigable prototype, a minimal viable product, and a complete project.

17. The system of claim 16 wherein the system is configured to display a group of different types of software applications comprising a social and photo centric type, a crowd sourced content type, leveraging simple device capabilities type, or location based type.

18. The system of claim 17 wherein the system is configured to allows the user to select the one or more types of operating system for which the desired customer software application is developed.

* * * * *